(12) United States Patent
Patel et al.

(10) Patent No.: US 11,690,708 B2
(45) Date of Patent: Jul. 4, 2023

(54) HEART VALVE DOCKING SYSTEM

(71) Applicant: Edwards Lifesciences Corporation, Irvine, CA (US)

(72) Inventors: Darshin S. Patel, San Juan Capistrano, CA (US); Hernan Altman, Kiryat Tivon (IL); Boaz Manash, Givat Ada (IL); Tamir S. Levi, Zikhron Yaakov (IL); Dinesh L. Sirimanne, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 239 days.

(21) Appl. No.: 16/902,612

(22) Filed: Jun. 16, 2020

(65) Prior Publication Data

US 2020/0306034 A1  Oct. 1, 2020

Related U.S. Application Data

(62) Division of application No. 15/684,836, filed on Aug. 23, 2017, now Pat. No. 10,687,938.

(Continued)

(51) Int. Cl.
*A61F 2/24* (2006.01)
*A61B 17/00* (2006.01)
*A61B 17/064* (2006.01)

(52) U.S. Cl.
CPC .......... *A61F 2/2409* (2013.01); *A61F 2/2412* (2013.01); *A61F 2/2418* (2013.01); *A61F 2/2427* (2013.01); *A61F 2/2436* (2013.01); *A61F 2/2466* (2013.01); *A61B 2017/00243* (2013.01); *A61B 2017/0649* (2013.01);
(Continued)

(58) Field of Classification Search
None
See application file for complete search history.

(56) References Cited

U.S. PATENT DOCUMENTS 4,035,849 A   7/1977   Angell et al.
4,781,704 A   11/1988  Potter
(Continued)

FOREIGN PATENT DOCUMENTS

CN   103957841 A   7/2014
CN   105682610 A   6/2016
(Continued)

*Primary Examiner* — Megan Y Wolf
(74) *Attorney, Agent, or Firm* — Edwards Lifesciences

(57) ABSTRACT

Methods of implanting docking devices for prosthetic valves at a native heart valve include positioning a distal end of a delivery catheter into a first chamber of a heart, advancing a tubular body of a docking device from within the delivery catheter so that the distal end of the tubular body is advanced between native valve leaflets and positioned in a second chamber of the heart. The methods further include inserting a coil into a lumen of the docking device so that the tubular body adopts a configuration, releasing a proximal end of the docking device in the first chamber, inserting a replacement valve in an inner space of the docking device, and radially expanding the replacement valve until there is a retention force between the replacement valve and the docking device to hold the replacement valve in a stable position in the native valve.

16 Claims, 13 Drawing Sheets

Related U.S. Application Data

(60) Provisional application No. 62/395,940, filed on Sep. 16, 2016, provisional application No. 62/380,117, filed on Aug. 26, 2016.

(52) U.S. Cl.
CPC .............. *A61F 2230/0008* (2013.01); *A61F 2230/0091* (2013.01); *A61F 2250/0036* (2013.01); *A61F 2250/0039* (2013.01)

(56) References Cited

U.S. PATENT DOCUMENTS

| | | |
|---|---|---|
| 4,790,843 A | 12/1988 | Carpentier et al. |
| 5,059,177 A | 10/1991 | Towne |
| 5,275,152 A | 1/1994 | Krauter et al. |
| 5,411,552 A | 5/1995 | Andersen et al. |
| 5,554,185 A | 9/1996 | Block et al. |
| 5,658,253 A | 8/1997 | Piontek et al. |
| 5,738,666 A | 4/1998 | Watson et al. |
| 5,762,637 A | 6/1998 | Berg et al. |
| 5,840,081 A | 11/1998 | Andersen et al. |
| 6,168,614 B1 | 1/2001 | Andersen et al. |
| 6,391,018 B1 | 5/2002 | Tanaka et al. |
| 6,405,414 B1 | 6/2002 | Byrnes et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,458,153 B1 | 10/2002 | Bailey et al. |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,121 B2 | 5/2004 | Ortiz et al. |
| 6,797,002 B2 | 9/2004 | Spence et al. |
| 6,908,481 B2 | 6/2005 | Cribier |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Fremulis et al. |
| 7,125,421 B2 | 10/2006 | Tremulis et al. |
| 7,314,485 B2 | 1/2008 | Mathis |
| 7,377,941 B2 | 5/2008 | Rhee et al. |
| 7,445,632 B2 | 11/2008 | McGuckin, Jr. et al. |
| 7,585,321 B2 | 9/2009 | Cribier |
| 7,618,446 B2 | 11/2009 | Andersen et al. |
| 7,637,946 B2 | 12/2009 | Solem et al. |
| 7,708,775 B2 | 5/2010 | Rowe et al. |
| 7,737,060 B2 | 6/2010 | Strickler et al. |
| 7,740,614 B2 | 6/2010 | Murashita et al. |
| 7,785,366 B2 | 8/2010 | Maurer et al. |
| 7,857,770 B2 | 12/2010 | Raulerson et al. |
| 7,942,927 B2 | 5/2011 | Kaye et al. |
| 7,951,195 B2 | 5/2011 | Antonsson et al. |
| 8,128,691 B2 | 3/2012 | Keranen |
| 8,142,492 B2 | 3/2012 | Forster et al. |
| 8,182,529 B2 | 5/2012 | Gordon et al. |
| 8,236,049 B2 | 8/2012 | Rowe et al. |
| 8,323,335 B2 | 12/2012 | Rowe et al. |
| 8,360,988 B2 | 1/2013 | Bobo, Sr. et al. |
| 8,377,115 B2 | 2/2013 | Thompson |
| 8,388,680 B2 | 3/2013 | Starksen et al. |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,454,683 B2 | 6/2013 | Rafiee et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,801,776 B2 | 8/2014 | House et al. |
| 8,864,823 B2 | 10/2014 | Cartledge et al. |
| 8,931,637 B2 | 1/2015 | Deeds |
| 9,078,747 B2 | 7/2015 | Conklin |
| 9,095,434 B2 | 8/2015 | Rowe |
| 9,096,368 B2 | 8/2015 | Wu |
| 9,119,718 B2 | 9/2015 | Keranen |
| 9,192,471 B2 | 11/2015 | Bolling |
| 9,237,886 B2 | 1/2016 | Seguin et al. |
| 9,314,335 B2 | 4/2016 | Konno |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| D809,136 S | 1/2018 | Kirwan, Jr. |
| 2002/0032481 A1 | 3/2002 | Gabbay |
| 2002/0107535 A1 | 8/2002 | Wei et al. |
| 2002/0151970 A1 | 10/2002 | Garrison et al. |
| 2002/0165569 A1 | 11/2002 | Poor et al. |
| 2003/0225420 A1 | 12/2003 | Wardle |
| 2004/0111006 A1 | 6/2004 | Alferness et al. |
| 2004/0193260 A1 | 9/2004 | Alferness et al. |
| 2004/0260389 A1 | 12/2004 | Case et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137691 A1 | 6/2005 | Salahieh et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2006/0195134 A1 | 8/2006 | Crittenden |
| 2006/0229561 A1 | 10/2006 | Huszar |
| 2007/0010877 A1 | 1/2007 | Salahieh et al. |
| 2007/0027533 A1 | 2/2007 | Douk |
| 2007/0203575 A1 | 8/2007 | Forster et al. |
| 2007/0265700 A1 | 11/2007 | Eliasen et al. |
| 2007/0293808 A1 | 12/2007 | Williams et al. |
| 2008/0033542 A1 | 2/2008 | Antonsson et al. |
| 2008/0077235 A1 | 3/2008 | Kirson |
| 2008/0125853 A1 | 5/2008 | Bailey et al. |
| 2008/0172034 A1 | 7/2008 | Patton |
| 2008/0172035 A1 | 7/2008 | Starksen et al. |
| 2008/0208330 A1 | 8/2008 | Keranen |
| 2009/0192601 A1 | 7/2009 | Rafiee et al. |
| 2009/0319037 A1 | 12/2009 | Rowe et al. |
| 2010/0036484 A1 | 2/2010 | Hariton et al. |
| 2010/0145440 A1 | 6/2010 | Keranen |
| 2010/0312333 A1 | 12/2010 | Navia et al. |
| 2010/0318184 A1 | 12/2010 | Spence |
| 2012/0059458 A1 | 3/2012 | Buchbinder et al. |
| 2012/0123529 A1 | 5/2012 | Levi et al. |
| 2012/0197379 A1 | 8/2012 | Laske et al. |
| 2012/0283820 A1 | 11/2012 | Tseng et al. |
| 2013/0006352 A1 | 1/2013 | Yaron |
| 2013/0190862 A1 | 7/2013 | Pintor et al. |
| 2013/0190865 A1 | 7/2013 | Anderson |
| 2013/0304197 A1 | 11/2013 | Buchbinder et al. |
| 2014/0074299 A1 | 3/2014 | Endou et al. |
| 2014/0081394 A1 | 3/2014 | Keranen et al. |
| 2014/0172070 A1 | 6/2014 | Seguin |
| 2014/0214159 A1 | 7/2014 | Vidlund et al. |
| 2014/0324163 A1 | 10/2014 | Keranen et al. |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0039082 A1 | 2/2015 | Keranen |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0228247 A1 | 8/2016 | Maimon et al. |
| 2016/0256276 A1 | 9/2016 | Yaron |
| 2016/0346080 A1 | 12/2016 | Righini et al. |
| 2017/0007399 A1 | 1/2017 | Keranen |

(56) References Cited

U.S. PATENT DOCUMENTS

| | | |
|---|---|---|
| 2017/0007402 A1 | 1/2017 | Zerkowski et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2018/0000580 A1 | 1/2018 | Wallace et al. |
| 2018/0085217 A1 | 3/2018 | Lashinski et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2019/0021859 A1* | 1/2019 | O'Carrol ............... A61F 2/2445 |

FOREIGN PATENT DOCUMENTS

| | | | |
|---|---|---|---|
| CN | 110290763 A | 9/2019 | |
| DE | 19532846 A1 | 3/1997 | |
| DE | 19907646 A1 | 8/2000 | |
| EP | 0592410 B1 | 10/1995 | |
| EP | 0850607 A1 | 7/1998 | |
| EP | 1432369 A1 | 6/2004 | |
| EP | 1521550 A2 | 4/2005 | |
| EP | 1296618 B1 | 1/2008 | |
| EP | 1827314 B1 | 12/2010 | |
| EP | 2620125 A1 | 7/2013 | |
| EP | 2726018 A2 | 5/2014 | |
| EP | 2806829 A2 | 12/2014 | |
| JP | 2015502194 A | 1/2015 | |
| JP | 2019511382 A | 4/2019 | |
| WO | 9117720 A1 | 11/1991 | |
| WO | 0149213 A2 | 7/2001 | |
| WO | 0154625 A1 | 8/2001 | |
| WO | 0247575 A2 | 6/2002 | |
| WO | 03020179 A1 | 3/2003 | |
| WO | 03028558 A2 | 4/2003 | |
| WO | 2005084595 A1 | 9/2005 | |
| WO | 2006011127 A2 | 2/2006 | |
| WO | 2005102015 A3 | 4/2007 | |
| WO | 2007067942 A1 | 6/2007 | |
| WO | 2008048626 A2 | 4/2008 | |
| WO | 2009155561 A2 | 12/2009 | |
| WO | 2010121076 A2 | 10/2010 | |
| WO | 2012027116 A1 | 3/2012 | |
| WO | 2012063228 A1 | 5/2012 | |
| WO | 2013068542 A1 | 5/2013 | |
| WO | 2013110722 A2 | 8/2013 | |
| WO | 2013114214 A2 | 8/2013 | |
| WO | 2015023579 A1 | 2/2015 | |
| WO | 2015023862 A2 | 2/2015 | |
| WO | 2015127264 A1 | 8/2015 | |
| WO | 2015198125 A1 | 12/2015 | |
| WO | 2016038017 A1 | 3/2016 | |
| WO | 2016040881 A1 | 3/2016 | |
| WO | 2016101529 A1 | 6/2016 | |
| WO | 2016130820 A1 | 8/2016 | |
| WO | 2017103833 A1 | 6/2017 | |
| WO | 2018118717 A1 | 6/2018 | |
| WO | 2018222799 A1 | 12/2018 | |

* cited by examiner

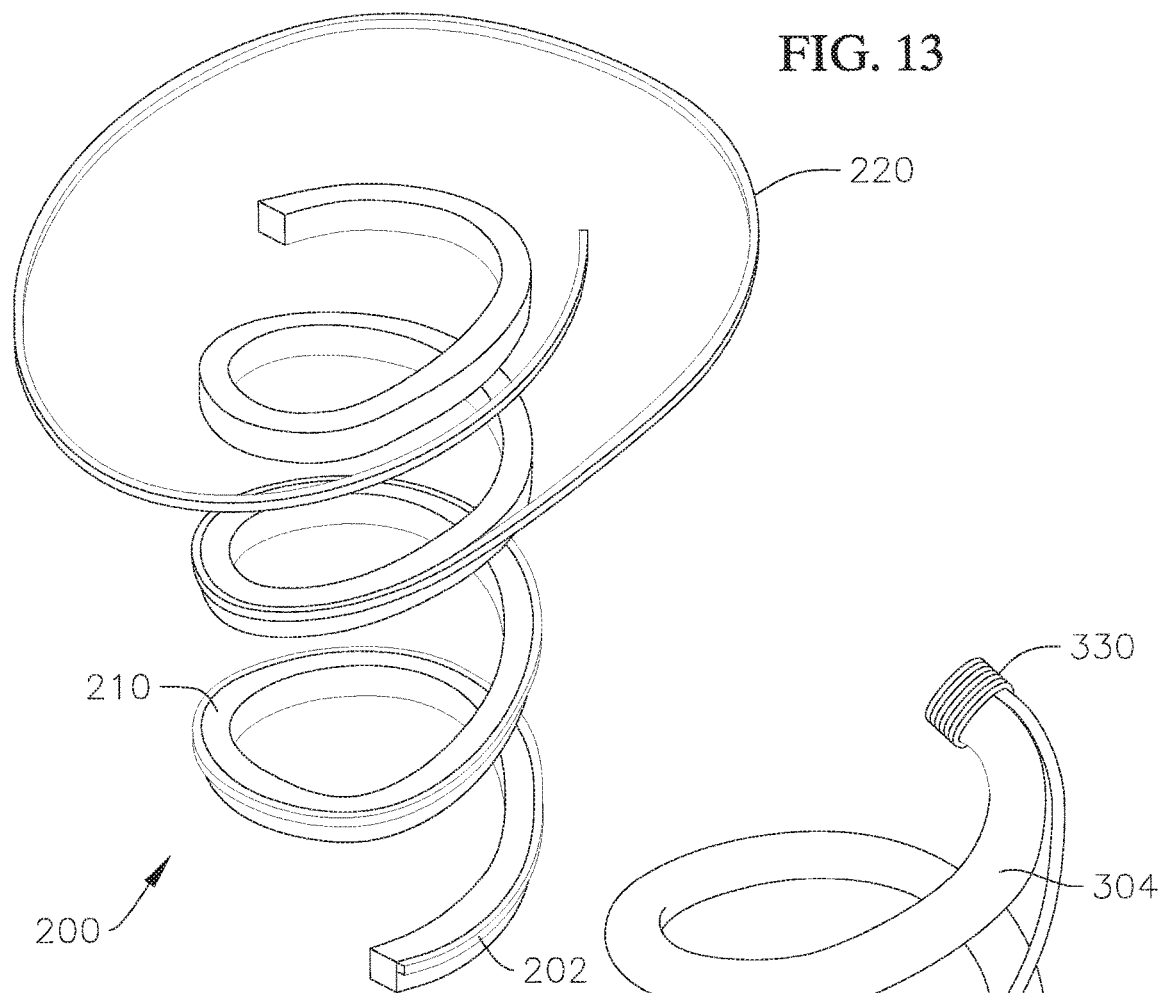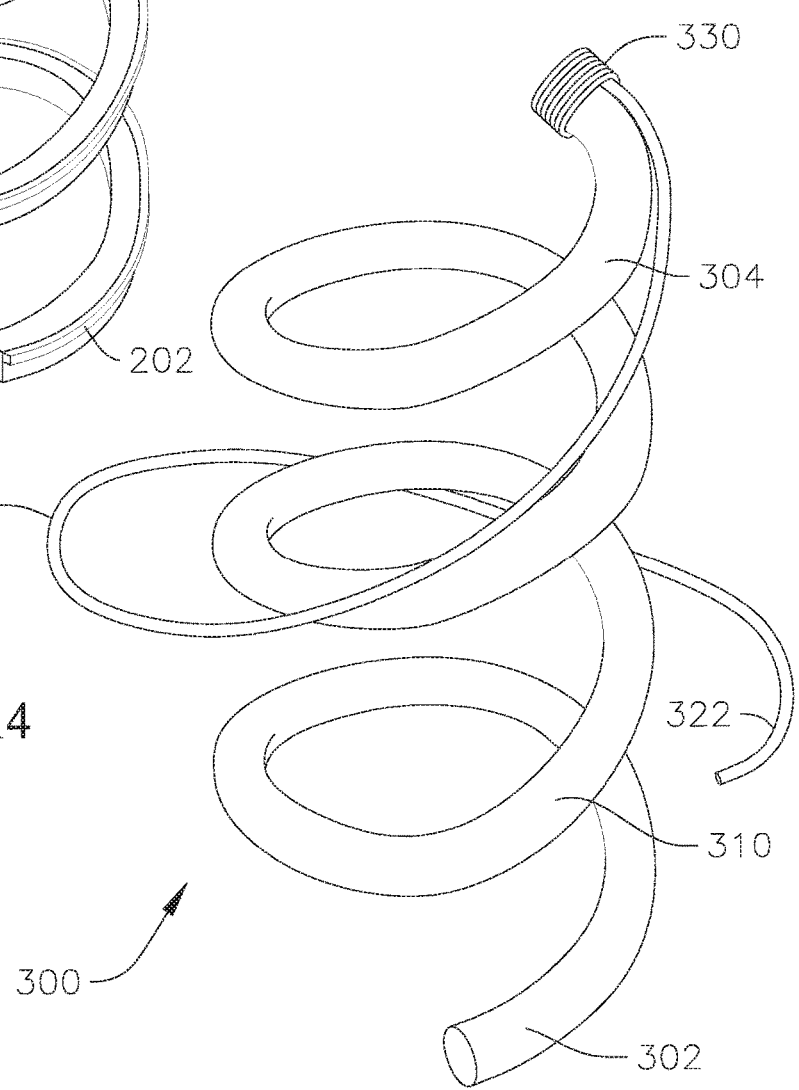

HEART VALVE DOCKING SYSTEM

CROSS-REFERENCE TO RELATED APPLICATIONS

This application is a divisional of U.S. patent application Ser. No. 15/684,836, filed on Aug. 23, 2017, which claims priority to U.S. Provisional Patent Application No. 62/380,117, filed on Aug. 26, 2016 and U.S. Provisional Patent Application No. 62/395,940, filed on Sep. 16, 2016. Each of the foregoing applications as well as U.S. patent application Ser. No. 14/372,953, entitled "Mitral Valve Docking Devices, Systems, and Methods," filed on Jul. 17, 2014 and U.S. patent application Ser. No. 15/682,287, filed on Aug. 21, 2017 are all incorporated herein by reference in their entireties.

FIELD OF THE INVENTION

The invention generally relates to medical devices and procedures pertaining to prosthetic heart valves. More specifically, the invention relates to the replacement of heart valves that may be dysfunctional or have malformations. Embodiments of the invention relate to an anchoring or docking device that can hold and maintain a positioning of a prosthetic heart valve therein, to replace the function of a native heart valve, for example, for a mitral or tricuspid valve replacement procedure. Embodiments of the invention also relate to implantation procedures associated with such anchoring or docking devices, or with assemblies including such an anchoring device and the prosthetic heart valve.

BACKGROUND

Description of Related Art

Referring first to FIGS. 1 and 2, the mitral valve 50 controls the flow of blood between the left atrium 52 and the left ventricle 54 of a human heart. After the left atrium 52 receives oxygenated blood from the lungs via the pulmonary veins, the mitral valve 50 permits the flow of the oxygenated blood from the left atrium 52 into the left ventricle 54. Subsequently, the left ventricle 54 contracts, and the oxygenated blood that is being held in the left ventricle is delivered through the aortic valve 56 and the aorta 58 to the rest of the body. Meanwhile, during this ventricular contraction, the mitral valve should close to prevent any of the blood that was being held in the left ventricle from flowing back into the left atrium.

When the left ventricle contracts, the blood pressure in the left ventricle increases substantially, which serves to urge the mitral valve closed. Due to the large pressure differential between the left ventricle and the left atrium during this time, a large amount of pressure is placed on the mitral valve, leading to a possibility of prolapse, or eversion of the leaflets of the mitral valve back into the left atrium. To prevent this, a network of chordae tendineae 62 connects the leaflets of the mitral valve to papillary muscles located on the walls of the left ventricle, where both the chordae tendineae and the papillary muscles are tensioned during ventricular contraction to hold the leaflets of the mitral valve in the closed position and to prevent them from turning inside-out and extending back towards the left atrium, thereby preventing backflow of the oxygenated blood into the left atrium. The network of chordae tendineae 62 is schematically illustrated in both the heart cross-section of FIG. 1 and the mitral valve of FIG. 2, the latter of which also shows a general shape of the mitral valve and its leaflets as viewed from the left atrium. Commissures 64 are located at the ends of the mitral valve 50 where the anterior leaflet 66 and the posterior leaflet 68 come together.

Various complications of the mitral valve and other valves can cause potentially fatal heart disease. One form of valvular heart disease is mitral valve leak or mitral regurgitation, characterized by an abnormal leaking of blood from the left ventricle through the mitral valve back into the left atrium. This can be caused, for example, by dilation of the heart, weakening of the chordae tendineae and/or the papillary muscles, or by damage to the native leaflets. In these circumstances, it can be desirable to repair the native valve or to replace the functionality of the native valve with that of a prosthetic heart valve.

With respect to mitral valve replacement, historically there has been less research and development directed towards commercially available ways to replace a mitral valve through a transcatheter approach and/or other minimally or less invasive procedures. Mitral valve and tricuspid valve replacement can be more difficult than aortic valve replacement in many respects, for example, due to the non-circular physical shape of the mitral valve, its sub-annular anatomy, and more difficult access to the valve due to its position deeper in the heart.

It could be beneficial to use prosthetic aortic valves or similar circular or cylindrical valve prostheses for mitral and tricuspid valve replacements as well. However, one issue with replacing mitral valves in this manner is the size and non-circular shape of the native mitral annulus, as seen in FIG. 2. Aortic valves are more circular in shape, so prosthetic transcatheter aortic valves also have more circular or cylindrical valve frames. Further, in many aortic valve replacement cases, the need for valve replacement arises from aortic valve stenosis, where the aortic valve narrows due to calcification or other hardening of the native leaflets. Therefore, in these cases, the aortic annulus generally provides a naturally circular, compact, and stable anchoring site for prosthetic valves.

On the other hand, the mitral and tricuspid valves are both larger than the aortic valve, and more elongate in shape, making them more difficult and unconventional sites for implanting a replacement valve with a generally circular or cylindrical valve frame. A circular prosthetic valve that is too small can result in leaking around the implant (i.e., paravalvular leakage) if a good seal is not established around the valve, while a circular prosthetic valve that is too large can stretch out and damage the narrower parts of the native mitral annulus.

Another prominent obstacle to effective mitral valve replacement stems from the large cyclic loads that the replacement valve will be subjected to, and the need to establish a sufficiently strong and stable anchoring or retention of the prosthetic valve in the mitral annulus that can withstand such forces without dislodging, especially from heart movement and/or pressures applied on the implant during ventricular contraction. In addition, such movement and rhythmic loads can easily fatigue the implant, leading to fractures or other damage to the valve. And if the valve prosthesis manages to remain held at the mitral position, even a slight shift in the alignment of the valve can still lead to blood flow through the valve or other parts of the heart (e.g., left ventricular outflow tract) being obstructed or otherwise negatively impacted.

SUMMARY

One way to apply existing circular or cylindrical transcatheter valve technology to non-circular valve replacement (e.g., mitral valve replacement) is to use an anchoring or docking station or other docking device that forms or otherwise provides a more circular docking site at the native valve position to hold the prosthetic valve. Existing expandable transcatheter valves that were developed for the aortic position, or similar valves that have been slightly modified to more effectively replicate valve function other than aortic valve function, can then be more securely implanted at the native valve position using such docking stations. Such docking stations can first be positioned at the native valve annulus, and thereafter, the valve implant can be advanced and positioned through the docking station while in a collapsed configuration, and can then be expanded, for example, via balloon expansion, self-expansion (e.g., when the frame is made of a shape memory material, such as NiTi), or mechanical expansion, so that the frame of the valve implant pushes radially against the docking station to hold the valve implant in place. Preferably, the docking station can be delivered using minimally or less invasive techniques, such as the same or similar transcatheter approaches used to deliver the valve implants, so that the docking device and the valve implant do not need to be delivered using completely separate and/or independent procedures.

It would therefore be desirable to provide devices and methods for facilitating the docking or anchoring of such replacement valves. Embodiments herein provide a stable docking station or docking device for retaining a prosthetic valve. Other features are provided in order to improve or ease the delivery of the docking device, to hold a desired position of the docking device after it has been advanced to a desired position at the implant site and prior to delivery of the prosthetic valve, and/or to improve retention of the prosthetic valve by the docking device after expansion of the valve therein. Such docking devices and methods can, in some instances, be used in the mitral position, but can also be used for other valve replacement procedures, for example, for tricuspid, pulmonary, or aortic valve replacements, to provide for more secure and robust anchoring and holding of valve implants at the native annuluses at those positions as well.

Docking devices for docking a prosthetic valve or valve prosthesis at a native valve of a heart and systems including such docking devices are disclosed. Docking devices can include a flexible body with one or more lumens extending through the flexible body (for example, a first lumen extending through the flexible body and a second lumen extending through the flexible body). The docking device(s) can also include one or more coils (for example, a first coil and a second coil). The flexible body can have a tubular structure and the one or more lumens (e.g., the first lumen and the second lumen) can each extend fully or at least partially through the flexible body. The flexible body or tubular structure can have at least one full or partial central turn, have another shape, or have no particular pre-set shape (e.g., a simple straight tube). The one or more lumens can each have one or more cross-sectional dimensions (e.g., area, diameter, width, etc.). For example, the first lumen can have a first cross-sectional area and the second lumen can have a second cross-sectional area.

The one or more coils can be more rigid than the flexible body and can each be configured to fit within one of the one or more lumens. The one or more coils can each have a plurality of circular turns that each define a diameter (e.g., a coil diameter or diameter of an inner space partially or fully circumscribed by one or more of the turns), which diameter can be the same as or different from diameters of other coils. For example, when a first coil and a second coil are used, the first coil can be more rigid than the flexible body, can be configured to fit within the first lumen, and can have a plurality of circular turns that define a first diameter. Similarly, the second coil can also be more rigid than the flexible body, can be configured to fit within the second lumen, and can have a plurality of circular turns that define a second diameter, which is less than the first diameter.

The docking devices and coils described herein can each have multiple configurations, e.g., straightened or elongated delivery configurations, unconstrained or relaxed configurations, deployed or implanted configurations, transition configurations, combinations of these, etc.) and the configurations can have different shapes, sizes, diameters, etc.

For example, a docking device can have at least a first configuration and a second configuration. In one example, the first configuration can be adopted or formed when the first coil is inserted through or positioned within (e.g., fully or at least partially within) the first lumen. In this first configuration the flexible body or docking device can define or have a third diameter (e.g., a coil diameter or diameter of an inner space partially or fully circumscribed by the flexible body or docking device). The second configuration can be adopted or formed when the second coil is inserted through or positioned within (e.g., fully or at least partially within) the second lumen. In this second configuration the flexible body or docking device can define or have a fourth diameter that is less than the first diameter and/or greater than the third diameter. In the first configuration, the third diameter can be greater than or equal to the first diameter (or less in some circumstances). In the second configuration, the fourth diameter can be less than the first diameter and greater than or equal to the second diameter (or less than the second diameter in some circumstances).

Any of the docking device(s), coils, and/or flexible bodies herein can also have an upper turn. The upper turn can be configured to extend in a proximal direction from other turns (e.g., from the plurality of turns). The upper turn(s) can be configured as a stabilization turn/coil to help prevent migration of the docking device (e.g., after implantation of the docking device but before implantation of the prosthetic valve). The upper turn(s) can define an upper turn diameter greater than a diameter in another region of the docking device, coil, and/or flexible body. An elliptical upper turn can have a major axis diameter (e.g., between 40-100 mm) and a minor axis diameter (e.g., between 20-80 mm), each greater than the first diameter. For example, the first coil can comprise an upper turn extending in a proximal direction from the plurality of turns, wherein the upper turn of the first coil is configured as a stabilization turn to help prevent migration of the docking device, the upper turn of the first coil defining an upper turn diameter greater than the first diameter.

Any of the docking device(s), coils, and/or flexible bodies herein can also comprise one or more coverings. For example, a high-friction cover on a portion of the flexible body configured such that slippage of the docking device relative to the native leaflets is inhibited when implanted. Optionally, the covering can have a large amount of surface area to promote tissue ingrowth.

Systems herein (e.g., systems for replacing a heart valve) can include a docking device. The docking device can be the same as or similar to the docking devices described above or elsewhere in this disclosure. For example, a docking device of a system can have a tubular body, a first coil, and a second coil, and an inner space defined by the docking device in its second configuration (e.g., a relaxed or implanted/deployed configuration) as described above. The system(s) can further include a replacement valve (e.g., a prosthetic valve). The replacement valve can have an expandable frame and a plurality of leaflets. The replacement valve can be configured to be inserted into the inner space of the docking device and expanded to an expanded configuration. In its expanded configuration, the replacement valve can be configured to apply an outward pressure to the docking device sufficient to maintain a stable position of the replacement valve within the inner space of the docking device and/or relative to the native valve anatomy (e.g., native annulus, native leaflets, etc.). Some of the native anatomy (e.g., native leaflets, chordae, etc.) can be trapped or squeezed between the docking device and the replacement valve when deployed/ implanted.

Docking devices herein for docking a prosthetic valve or valve prosthesis at a native heart valve can include one or more coils/coil portions connected to each other. For example, a docking device can have a first coil having a proximal end, a distal end, and a plurality of turns that extend between the proximal and distal ends. The docking device can also have a second coil having a proximal end, a distal end, and at least one turn (e.g., a half-rotation turn, a full-rotation turn, a plurality of turns, between one half to 5 full-rotation turns). The at least one turn or turns can extend between the proximal and distal ends of the second coil. The second coil can be located at or proximate the distal end, proximal end, or another portion of the second coil.

A portion of the first coil can be in contact with a portion of the second coil (e.g., they can meet at a fork/split/ junction). The first coil and the second coil can be integrally formed with one another or can be formed as separate coils that are connected to one another. In one embodiment, the second coil can be connected to the first coil near the proximal end of the first coil, and can extend away from the first coil towards the distal end of the first coil. In one embodiment the second coil can be connected to the first coil near the distal end of the first coil, and the second coil can extend alongside in contact with the first coil in a distal region, and the second coil can split away from the first coil towards the proximal end of the first coil.

Systems herein can include a docking device having one or more coils or coiled portions connected to each other, for example, a docking device the same as or similar to the docking devices described above or elsewhere in this disclosure. For example, a docking device of a system can have a first coil and a second coil connected at least at one point. The system(s) can also have a replacement valve, for example, a replacement valve as described above or elsewhere herein. For example, a replacement valve having an expandable frame and a plurality of leaflets. In an expanded configuration, the replacement valve can be configured to apply an outward pressure to the docking device sufficient to maintain a stable position of the replacement valve within the inner space of the docking device and/or relative to the native valve anatomy (e.g., native annulus, native leaflets, etc.). As discussed above, some of the native anatomy (e.g., native leaflets, chordae, etc.) can be trapped or squeezed between the docking device and the replacement valve when deployed/implanted.

Methods are also described herein (e.g., methods of replacing a native valve, of treating a patient, of implanting a docking device at a native heart valve, etc.). Methods herein can include obtaining a docking device, for example, obtaining any of the docking devices disclosed above or elsewhere in this disclosure. For example, a docking device comprising a flexible tubular body having a distal end, a proximal end, a first lumen therethrough, and a second lumen therethrough. The method(s) can include inserting a delivery catheter through vasculature and/or one or more chambers of a heart, and/or positioning a distal end of a delivery catheter in a first location in the circulatory system (e.g., in vasculature or in a chamber of a heart, such as a left atrium, right atrium, etc.). The method(s) can include advancing the docking device (e.g., all or a portion of the docking device; the distal end of the docking device; etc.) from within the delivery catheter so that the distal end is advanced through or between the native valve leaflets (e.g., the mitral valve leaflets, tricuspid valve leaflets, etc.) and, if applicable, advancing the distal end around some or all of the chordae tendinae that may be present, and positioning the distal end of the docking device in a second location in the circulatory system (e.g., in vasculature or in a second chamber of the heart, such as the left ventricle, right ventricle, etc.).

A first coil, which can be the same as or similar to other coils described in this disclosure (e.g., comprising a plurality of turns and having a first diameter), can be inserted into the first lumen of a docking device including one or more lumens (e.g., fully or partially into the lumen), so that the tubular body adopts a first configuration. Insertion of the first coil into the first lumen can occur before or after advancing the tubular body from within the delivery catheter. Where insertion of the first coil into the first lumen occurs before the step of advancing the tubular body from within the delivery catheter, at least a portion of the tubular body and at least a portion of the first coil can be advanced together between the native valve leaflets and positioned in the second location (e.g., in the second chamber of the heart). Also, the step of inserting the first coil into the first lumen can occur before or after the step of positioning the distal end of a delivery catheter into the first chamber. Optionally, the first coil can come pre-loaded (e.g., packaged) in the tubular body, such that the end user or health care professional does not need to insert the first coil into the tubular body. If pre-loaded, the first coil can be permanently or removably connected or disposed in the tubular body.

The method(s) can include inserting second coil (which can be the same as or similar to other coils described in this disclosure) having a second diameter into a second lumen of the tubular body or docking device, so that at least a portion of the tubular body adopts a second configuration.

The method(s) can include releasing a proximal end of the docking device the first location (e.g., in the first chamber, such as the left atrium, right atrium, etc.). This can be done, for example, by retracting the delivery catheter proximally relative to the docking device.

The method(s) can include inserting a replacement valve in an inner space defined by the docking device/tubular body (e.g., when the docking device/tubular body is in the second configuration). The replacement valve can be radially expanded until there is a retention force between the replacement valve and the docking device to hold the replacement valve in a stable position relative to each other and/or relative to the native anatomy (e.g., one or more of the native valve, native annulus, native leaflets, etc.).

The method(s) (e.g., methods of replacing a native valve, of treating a patient, of implanting a docking device at a native heart valve, etc.) can also include steps for implanting one of docking devices disclosed herein that have one or more coils or coiled portions connected to each other (e.g., as discussed above and elsewhere in this disclosure). Steps used can include the same or similar steps to those discussed above or elsewhere herein. The method(s) can include obtaining a docking device. For example, the docking device can have a first coil having a plurality of turns and a second coil having a plurality of turns, wherein a portion of the first coil is in contact with a portion of the second coil.

The method(s) can include positioning a distal end of a delivery catheter in a first location in the circulatory system (e.g., in vasculature or in a first chamber of a heart, such as the left atrium, right atrium, etc. of a heart). The delivery catheter can contain the docking device in a first straightened configuration. A docking device can be advanced so that a distal end of at least the first coil is advanced through mitral valve leaflets, if applicable, around some or all of any chordae tendinae that may be present, and positioned in a second location in the circulatory system (e.g., in vasculature or in a second chamber of a heart, such as the left ventricle, right ventricle, etc.). The first and second coils of the docking device can adopt a pre-set shape of at least one full or partial circular turn. The first coil can have a first diameter and the second coil can have a second diameter. The method(s) can also include releasing a proximal end of the docking device in the second location (e.g., the first chamber, left atrium, right atrium, etc.).

The method(s) can also include inserting or positioning a replacement valve in an inner space defined by the docking device or tubular body in the second configuration. The method(s) can include radially expanding the replacement valve until there is a retention force between the replacement valve and the docking device to hold the replacement valve in a stable position. The connectivity of the coils of the docking device can be that of any of the embodiment described herein.

Various features and characteristics of systems and devices described elsewhere in this disclosure can be included in the systems and devices described here. Similarly, steps of procedures/methods described elsewhere in this disclosure can be included in the methods described here.

Valve replacement at the mitral position, as well as at other native valve positions, can be realized through the use of a coiled docking device that is first implanted at a native valve site for docking an expandable heart valve therein. Such coiled anchors or docking devices provide a more stable base in or against which the prosthetic valves can be expanded. Embodiments of the invention thus provide a more robust way to implant replacement heart valves, even at sites where the annulus itself is non-circular or otherwise variably shaped.

BRIEF DESCRIPTION OF THE DRAWINGS

Further features and advantages of the invention will become apparent from the description of embodiments using the accompanying drawings. In the drawings:

FIG. 13 shows a perspective view of an exemplary docking device;

FIG. 14 shows a perspective view of an exemplary docking device; and

DETAILED DESCRIPTION

Disclosed herein are various anchoring or docking devices which can be utilized in conjunction with implantation of prosthetic heart valves at native valve annuluses, to assist in more secure implantation of the prosthetic heart valves at the implant sites. Anchoring or docking devices according to embodiments of the invention provide a circular and/or stable annulus or docking region at the implant site, in which prosthetic valves having more circular cross-sections, e.g., cylindrically-shaped valve frames or stents, can be expanded or otherwise implanted. Some embodiments of the docking devices further include features which, for example, facilitate easier advancement of the docking devices around various anatomical features at or around the native valve, better hold a desired position of the docking devices prior to delivery of the prosthetic valves, and/or increase or otherwise improve retention of the prosthetic valves after they have been implanted in the docking devices. By providing such docking devices, replacement valves can be more securely implanted and held at any of various native valve annuluses, including at the mitral annulus.

Figure 5:
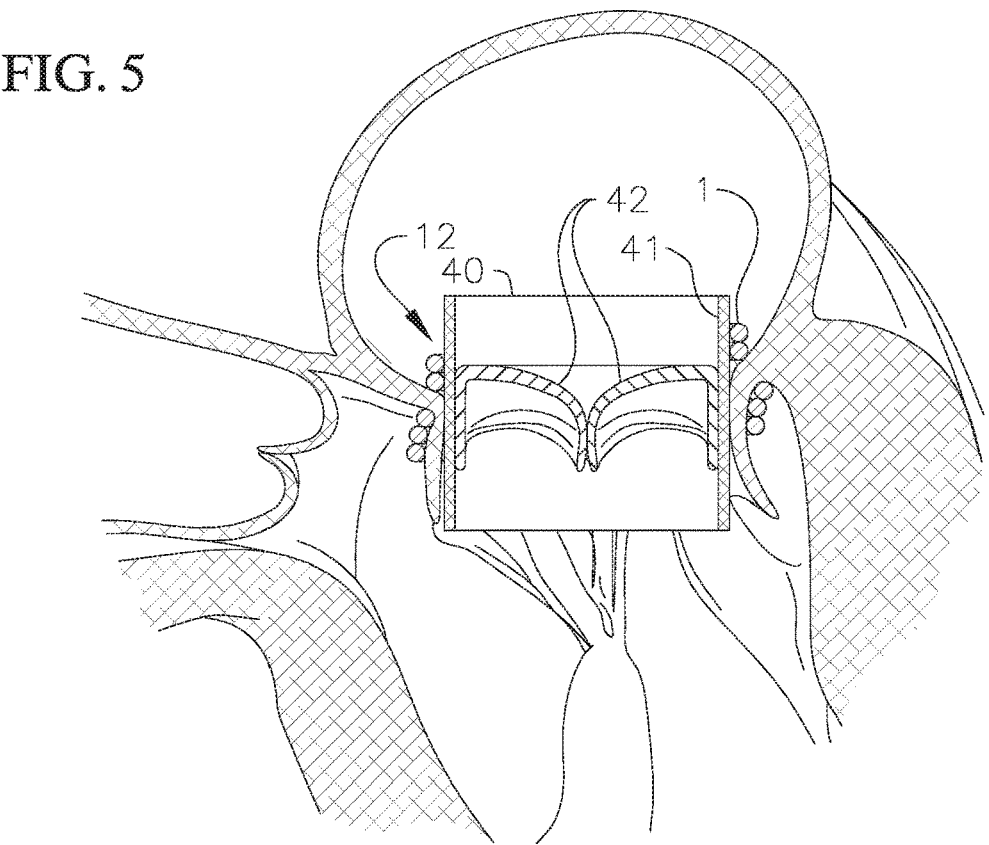
FIG. 5 shows a cross-sectional view of a portion of a heart with the docking device shown in FIGS. 3 and 4 and a prosthetic valve positioned in and being held by the docking device at the native mitral valve annulus.
Figure 6:
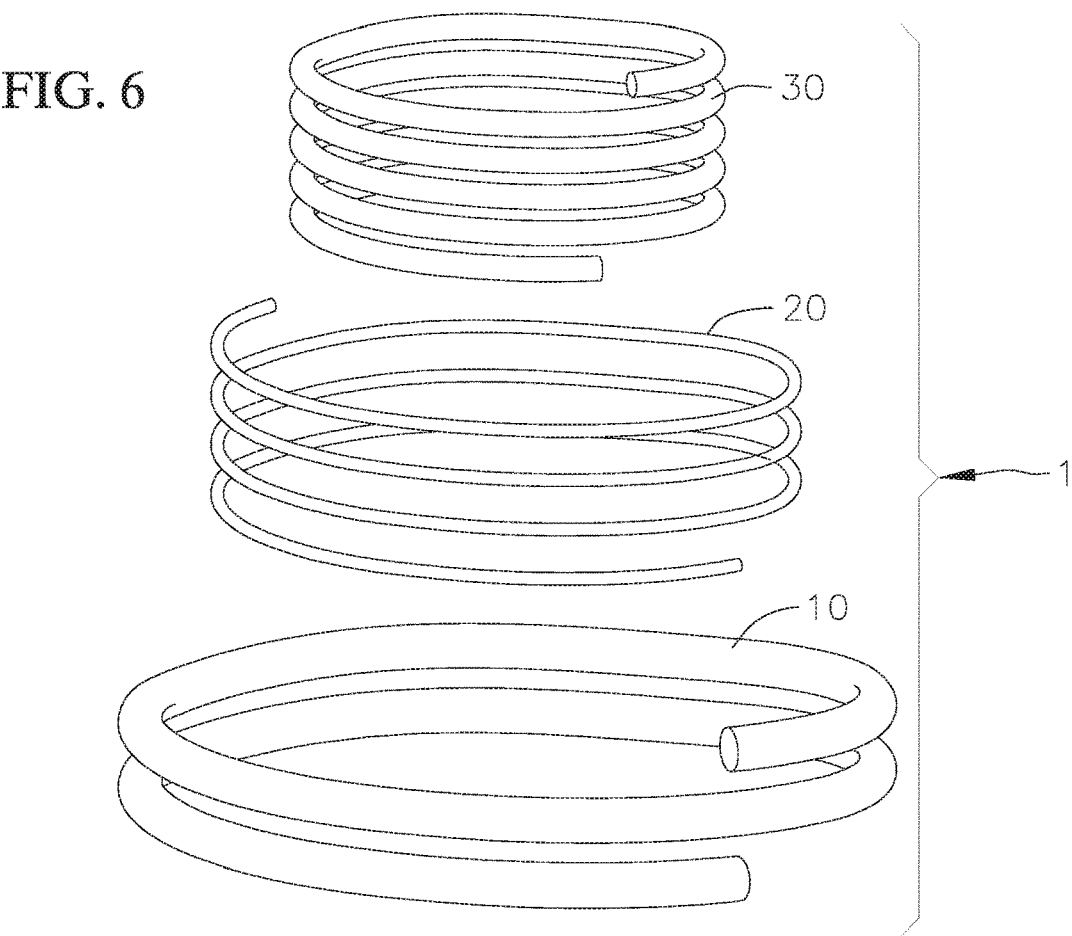
FIG. 6 shows a disassembled perspective view of an exemplary coil-shaped docking device for a prosthetic valve.
Figure 8:
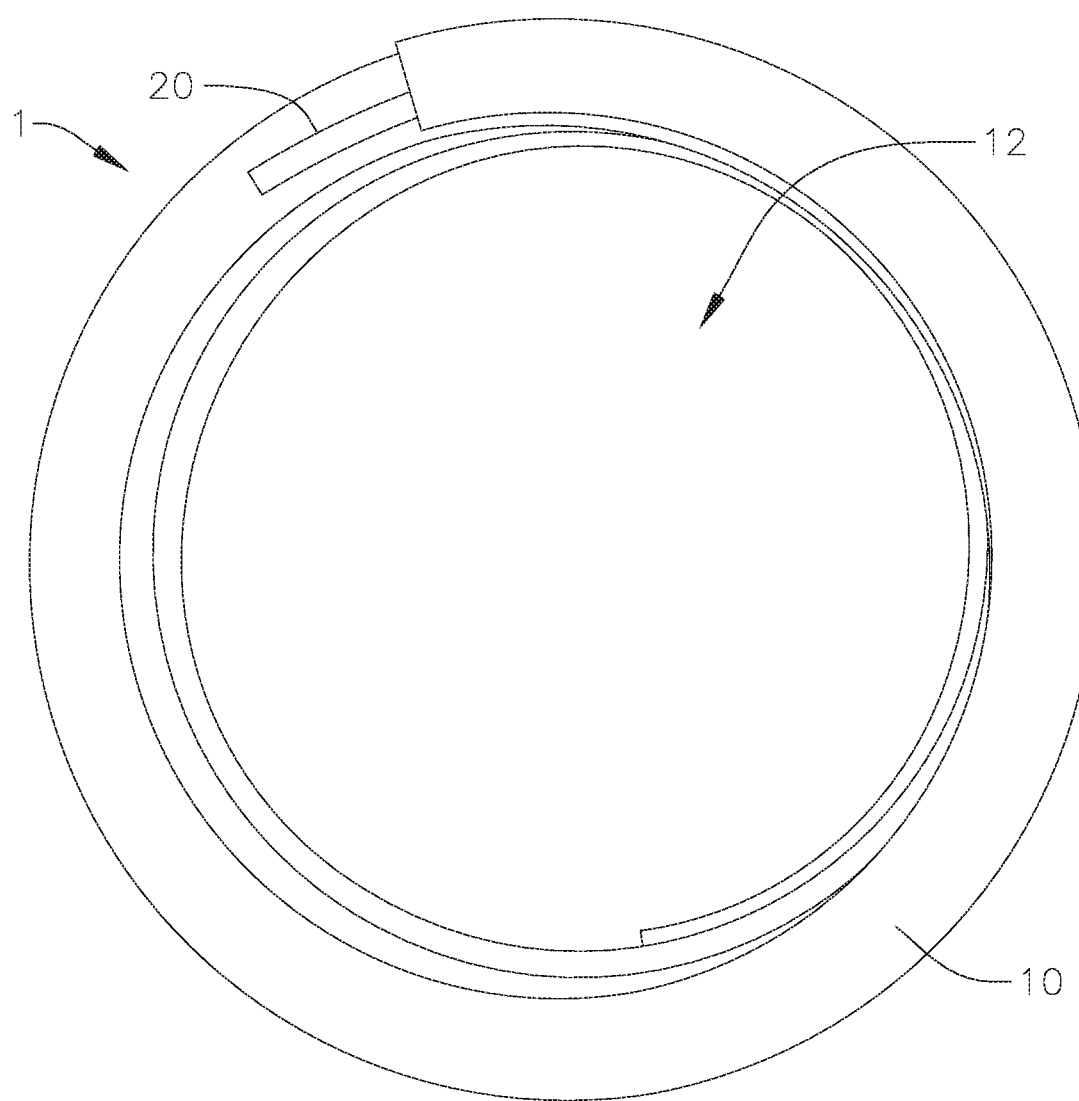
FIG. 8 shows a top perspective view of the docking device of FIG. 6, where the docking device assumes a first size.

Referring briefly first to FIGS. 6 and 8, an exemplary coil-shaped anchoring or docking device 1 includes a coiled body 10 having a plurality of turns that extend around a central axis of the docking device 1. At least a portion of the coiled body 10 of the docking device 1 extends helically, with the turns being generally circular and having substantially equal inner diameters. The turns of the coiled body 10 form an elongate inner space 12 that serves as a landing region or holding region for holding and retaining a prosthetic heart valve when the respective components (e.g., the anchoring or docking device and prosthetic valve, and/or any other components used) are implanted at a valve site, as can be seen, for example, in FIG. 5. Optionally, the turns can be circular, elliptical, ovoid, or another shape prior to the implantation of a replacement heart valve. A docking device can have various numbers of coil turns. For example, the number of central, functional, coil turns can range from just over a half turn (e.g., a half rotation) to 5 turns (e.g., 5 full rotations) or more, or one full turn to 5 turns. In an embodiment with three full turns, there can be an additional one half turn in the lower, ventricular, portion of the docking device. In one embodiment, there can be three full turns total in the docking device. In the upper, atrial, portion of the docking device, there can be one-half to three-fourths turn or more. While a range of turns is provided, as the number of turns in a docking device is decreased, the dimensions of the coil can also change to maintain a proper retention force. There can be one or a plurality of coils in a first chamber of the heart (e.g., the right or left atrium, etc.) and/or one or a plurality of coils in a second chamber of the heart (e.g., the right or left the ventricle, etc.).

The docking device 1 is positionable within the native valve, so that at least part of the coiled body 10 extends away from either side of the native valve or an annulus of the native valve. In a mitral or tricuspid application, part of the coiled body 10 is positioned in an atrium, and part of the coiled body 10 is positioned in a ventricle. In this manner, the prosthetic valve that is held in the docking device 1 can be implanted at roughly the same position as the native valve, while optionally being supported on both sides of the native valve or of an annulus of the native valve.

As such, at least a portion of the docking device 1 is passed through the native valve in one direction or the other (e.g., from ventricle to atrium, from atrium to ventricle, etc.). Due to the coiled or helical shape of the docking device 1, in some embodiments, a leading or distal end 2 of the docking device 1 can be rotated or inserted through the native valve and into a desired position prior to implantation of the prosthetic valve. For example, for mitral applications, the docking device 1 can be delivered to the mitral position via one of various access sites, for example, transatrially via the left atrium, transseptally through the atrial septum, or via one of various other known access sites or procedures. In still other embodiments, the docking device 1 can be inserted transapically or in a retrograde manner. For tricuspid applications, for example, the docking device 1 can be delivered using access sites to the right atrium (e.g., passing into the right atrium from the IVC or SVC) and/or right ventricle.

Figure 1:
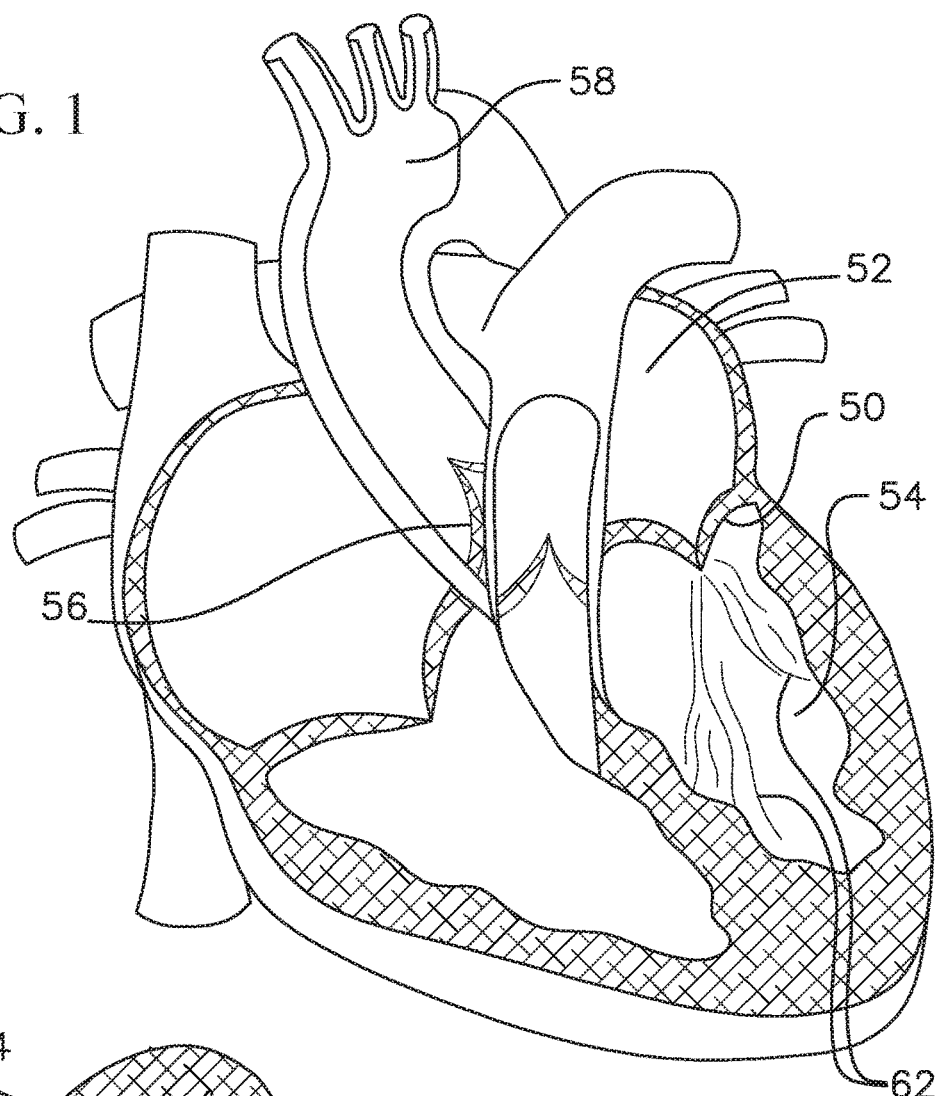
FIG. 1 shows a schematic cross-sectional view of a human heart.
Figure 2:
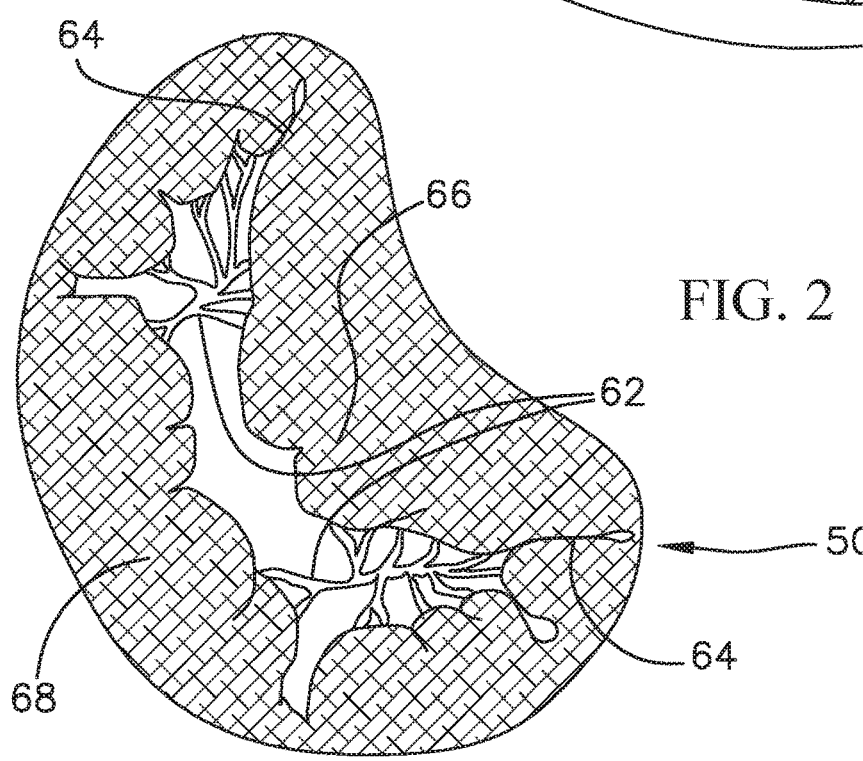
FIG. 2 shows a schematic top view of a mitral valve annulus of a heart.
Figure 3:
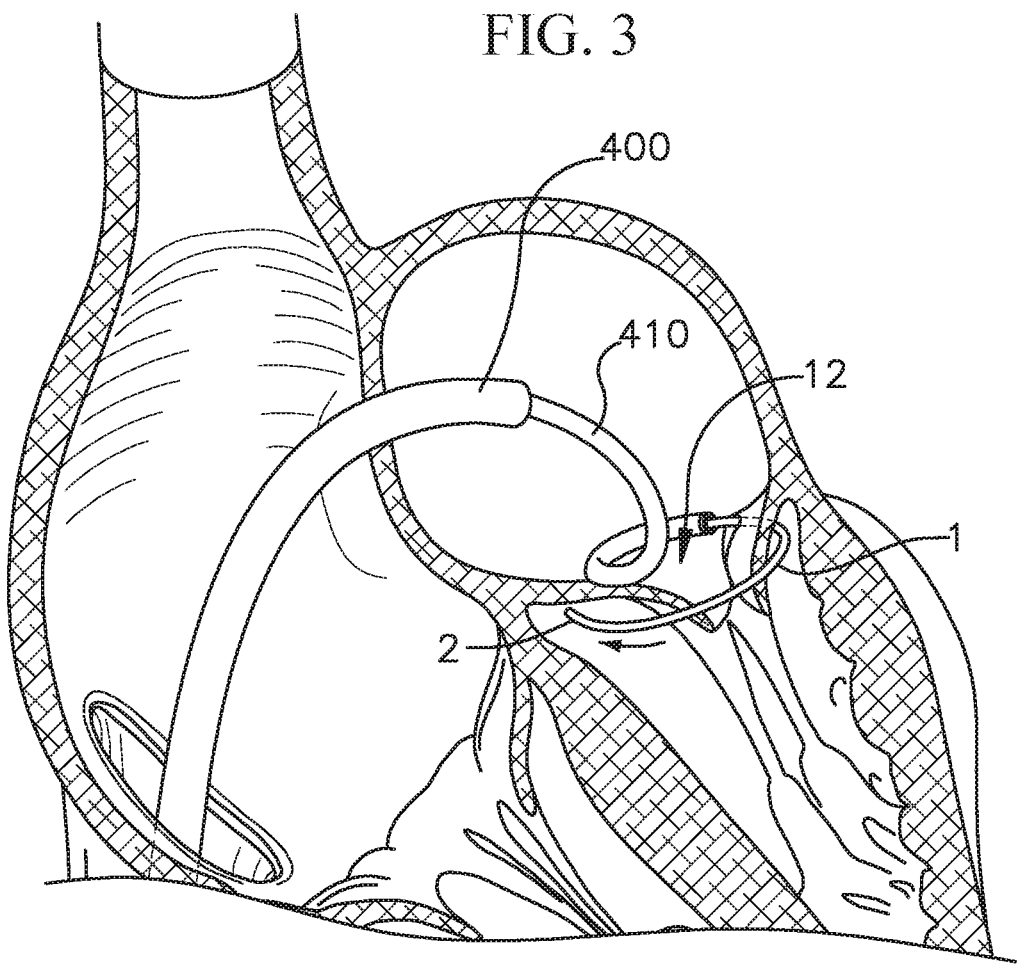
FIG. 3 shows a cross-sectional view of a portion of a heart during delivery of an exemplary coil-shaped docking device to a native mitral valve annulus of the heart.

FIG. 3 shows an exemplary implantation occurring at the mitral valve via a transseptal delivery method, where an incision or puncture is made in the atrial septum, and a guide sheath 400 and/or a delivery catheter 410 is advanced through the septum and into the left atrium of a patient's heart. In an exemplary procedure, the guide sheath 400 and/or delivery catheter 410 can first be introduced into the patient's venous system by percutaneous puncture and/or by a small surgical cut, for example, at the patient's groin, and then the guide sheath 400 and/or catheter 410 is advanced through the venous system to the right atrium. For exemplary tricuspid procedures, the anchoring or docking device 1 can be delivered from the right atrium to the tricuspid valve position, e.g., passing a portion of the docking device 1 through the native valve or a commissure of the native valve. For exemplary mitral procedures, as shown in FIG. 3, a distal end of the delivery catheter 410 can be passed from the right atrium through the atrial septum and positioned in the left atrium, with a distal opening of the delivery catheter 400 positioned just above the mitral plane near a desired access point (e.g., a commissure) through which the distal end 2 of the docking device 1 will be advanced into the left ventricle. In some procedures, the distal end of the delivery catheter 410 is positioned and directed towards commissure A3P3 of the native mitral valve, so that the docking device 1 can be advanced clockwise (i.e., looking in a direction of blood flow or in an inflow to outflow direction) through commissure A3P3 into the left ventricle. Other embodiments of docking devices can be wound or curved in the opposite direction, and instead be advanced through commissure A3P3 in a counter-clockwise direction into the left ventricle. In still other methods, the access point can instead be commissure A1P1, or any other portion of the opening defined by the mitral annulus, and the advancement can be either clockwise or counter-clockwise, depending on the situation. Also, the various docking devices and coils described herein can be configured to turn/wind either in a clockwise or counter-clockwise direction, even if only shown in the drawing as winding in one direction.

Where a guide sheath 400 is used, the guide sheath can be introduced and positioned in a desired position (e.g., crossing the septum as shown) prior to the delivery catheter 410, and the delivery catheter 410 can subsequently be inserted through a lumen of the guide sheath 400 and thereby be guided through the vasculature, right atrium, and/or left atrium, or the guide sheath 400 and delivery catheter 410 can be simultaneously introduced and positioned.

While the docking device 1 is held in the delivery catheter 410, the docking device 1 can be straightened to more easily maneuver through the delivery catheter 410 and for a smaller delivery profile. Thereafter, as the docking device 1 is advanced out of the delivery catheter 410, the docking device 1 can return to its original coiled or curved shape (e.g., a pre-set shape-memory shape). The docking device 1 can exhibit such properties, for example, by being made of or including a shape memory material (e.g., NiTi or another shape memory polymer or alloy), and then being shape set to a desired curvature that the docking device 1 reverts to during delivery. The distal end of the delivery catheter 410 can also assume a curved configuration with a curvature similar to the curvature of the docking device 1, to ease advancement of the docking device 1 out of the delivery catheter 400. The distal end 2 of the docking device 1 is then passed through the native mitral annulus (e.g., at a commissure) and into the left ventricle, where it is navigated around to encircle the native leaflets, the chordae tendineae, and any other desired mitral anatomy in the left ventricle, such that any of the native anatomy that is corralled by the docking device 1 will be positioned inside the inner space 12 of the docking device 1 once the docking device 1 has been advanced to a desired position. In tricuspid valve or other valve procedures, similar steps can be taken, but navigated according to that valves anatomy, e.g., a delivery catheter can be positioned near an access point (e.g., commissure) of the tricuspid valve and the docking device can be deployed such that it rotates around or encircles the native anatomy of the tricuspid valve. The docking device has enough flexibility to be pushed through a straight catheter, and enough structure so that it provides a sufficient retention force when deployed.

After a desired amount of the docking device 1 has been advanced into a chamber of the heart (e.g., the left ventricle, right ventricle, etc.), the rest of the docking device 1, for example the atrial side of the docking device 1 in the illustrated embodiment, can then be released into another chamber of the heart (e.g., the left atrium, right atrium, etc.). This can be accomplished, for example, by rotation of the distal end of the delivery catheter 410 in an opposite direction to the direction of advancement of the docking device 1 (not shown), so that the proximal side (e.g., atrial side) of the docking device 1 can be released without affecting the position of the distal side (e.g., ventricular side) of the docking device 1. If the docking device includes a stabilization turn/coil at the proximal side of the docking device, the stabilization turn/coil can be released such that it contacts surrounding anatomy (e.g., such that it contacts the walls of a chamber of the heart, atrium walls, walls of the circulatory system or vasculature, etc.) to stabilize or retain the docking device in a desired location/position prior to implantation of the prosthetic valve or THV.

Other methods can also be used to release the atrial side of the docking device 1 from the delivery catheter 400. For example, the docking device 1, if attached to the delivery catheter by suture, can be released from the delivery catheter 400 by releasing a suture lock as described in U.S. patent application Ser. No. 14/372,953, incorporated herein by reference in its entirety. For example, a long-release suture looped through an opening on a proximal end of the docking device, can be cut and then pulled to release the delivery catheter from the docking device once it is properly positioned. The suture can be cut or can be pulled through a loop, to release the docking device from the delivery catheter.

Figure 4:
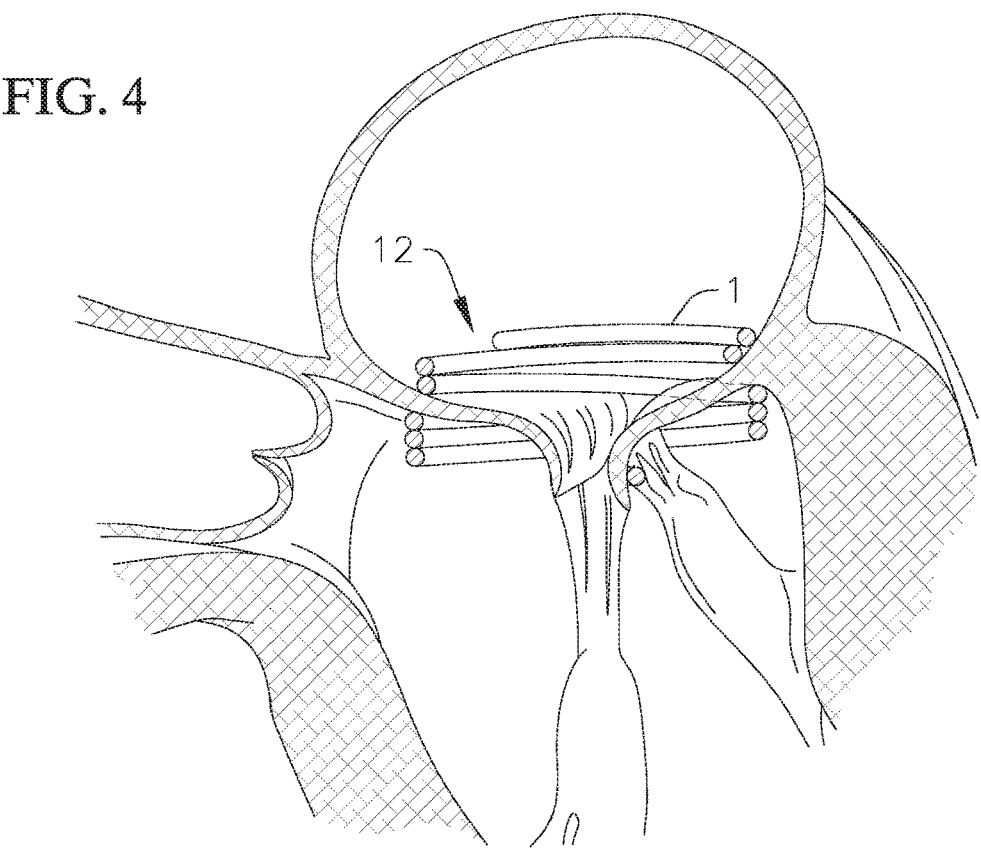
FIG. 4 shows a cross-sectional view of a portion of a heart with the exemplary docking device shown in FIG. 3 positioned at the native mitral valve annulus after delivery.

FIG. 4 shows a cross-sectional view of a portion of a patient's heart with the docking device 1 at the mitral position and prior to delivery of a prosthetic heart valve. In some procedures, during this time, the native mitral valve can still continue to operate substantially normally (or better, e.g., if the docking device helps improve coaptation), so that the patient remains stable. Similarly, the native tricuspid valve can still continue to operate substantially normally (or better, e.g., if the docking device helps improve coaptation) at a similar stage of implantation in the tricuspid valve position. Therefore, the procedure can be performed on a beating heart, without the need for a heart-lung machine, which also allows the practitioner more time flexibility to implant the valve prosthesis, without running the risk of the patient being in or falling into a position of hemodynamic compromise if too much time passes between the implantation of the docking device 1 and the later valve implantation.

With respect to embodiments the same as or similar to docking device 1 with one or more wires/coils that can be inserted into a tubular body 10 (or have a tubular coil 60 inserted around a coil 50, etc.), steps described below with regard to these embodiments can be used. For example a first wire/coil 20 (e.g., a smaller thickness wire with a larger coil diameter) can be inserted into the tubular body 10 to help the docking device be properly positioned in the native valve/anatomy, and later a second wire 30/coil (e.g., a larger thickness wire with a smaller coil diameter) can be inserted into the tubular body 10 to resize the functional coils or region for receiving the prosthetic valve, etc.

FIG. 5 shows a cross-sectional view of a portion of the heart with both the docking device 1 and a prosthetic valve 40 implanted at the mitral position. A similar arrangement can be had at other valve positions as well, e.g., at the tricuspid valve. The prosthetic valve 40 can be, for example, an expandable transcatheter heart valve (THV) that is delivered through a catheter in a radially collapsed state, and that is expanded after being advanced to a desired position in the inner space 12 of the docking device 1. In procedures/methods where a guide sheath 400 is used, the guide sheath 400 can create a channel through which other devices (e.g., the delivery catheter for delivering the prosthetic valve or THV, etc.) can also be delivered or navigated, e.g., after retraction and removal of the delivery catheter 410 for the docking device 1 from the guide sheath 400. Although, optionally, the guide sheath can be retracted and removed as well before a prosthetic valve or THV delivery catheter is navigated to the desired location for delivery of the prosthetic valve or THV. Such a THV or prosthetic valve 40 can have an expandable frame structure 41 housing a plurality of valve leaflets 42. The expandable frame 41 of the prosthetic valve 40 can be balloon expandable, can be self-expanding (e.g., by being made from a shape memory material such as NiTi), or can be expandable in one or more of various other mechanical or non-mechanical ways (e.g., via balloon expansion, etc.). There are numerous types of expandable prosthetic heart valves that would benefit from being anchored within the docking device 1, including those made by Edwards Lifesciences of Irvine, Calif., Medtronic of Minneapolis, Minn. and St. Jude Medical of Minneapolis, Minn. Upon expansion, the expandable frame 41 pushes radially outwardly and imparts a radially outward force against the docking device, and the docking device applies a radially inwardly directed counterforce against the prosthetic valve 40. In addition, some of the native anatomy (e.g., native leaflets, chordae, mitral anatomy, tricuspid anatomy, etc.) that was corralled by the docking device 1 and held in the inner space 12 is pinched or squeezed between the docking device 1 and the outer surface of the prosthetic valve 40 when the valve frame 41 is expanded. These interactions and opposing forces between the various components and anatomical features securely holds the entire assembly in place at the mitral position or other valve position. In non-circular embodiments of the docking device (e.g., having elliptical, ovoid, etc. coils), expansion of a circular prosthetic valve can cause the docking device coils to become more circular or circular in shape, as they conform to the shape of the prosthetic valve. The implantation procedure is then complete, and the delivery tools can be removed from the patient.

As shown above, to position and anchor itself to the native anatomy (e.g., mitral anatomy, tricuspid anatomy, etc.) both before and after implantation of a prosthetic valve 40, the docking device 1 relies on being navigated around and encircling the native leaflets, the chordae tendineae, and/or other parts of the native anatomy (e.g., mitral anatomy, tricuspid anatomy, etc.), which in turn contribute to holding the docking device 1 at a desired height and position at the native annulus (e.g., mitral annulus, tricuspid annulus, etc.). The mitral anatomy in an average patient spans approximately 50 mm along a long axis and 38 mm along a short axis. To adequately encircle the mitral anatomy (or other valve anatomy), the docking device can either have a size and dimensions similar to the size of the mitral anatomy (or other valve anatomy), or be adjustable during initial navigation around the mitral anatomy or other valve anatomy (e.g., with an articulable tip, adjustable size and/or shape, etc.), or both. On the other hand, in order for an expandable prosthetic heart valve to be effectively held in the docking device, the inner diameter of the inner space 12 of the docking device should be sufficiently small (e.g., smaller than an outer diameter of the prosthetic valve 40 in its unbiased expanded state, an example of which is about 29 mm) in order to generate sufficient retention forces between the docking device and the prosthetic valve.

In addition, it can also be beneficial to deploy and hold the docking device 1 at a relatively higher position at the native valve annulus. For example, in the above mitral application, deploying the docking device 1 as high as possible in the left ventricle also allows the prosthetic valve 40 to be held higher in the left ventricle.

Figure 7:
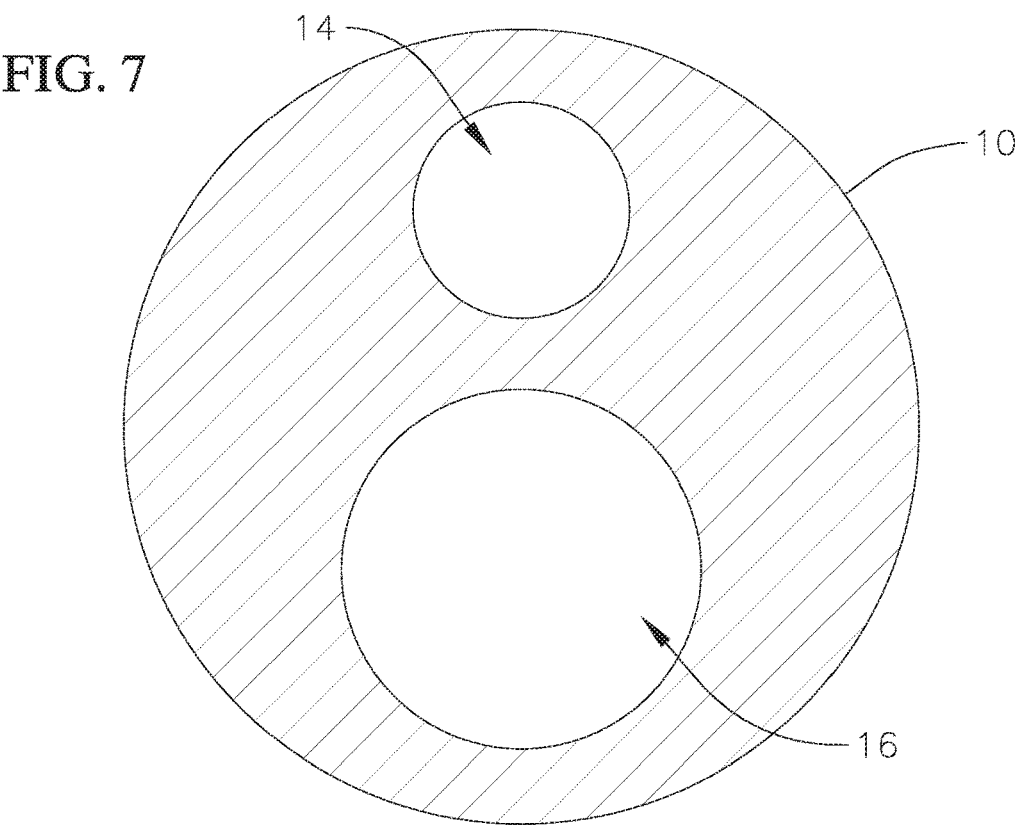
FIG. 7 shows a cross-sectional view of a tubular body of the docking device of FIG. 6.

Referring to FIG. 6, an exemplary docking device 1 can include a body 10, a first wire/coil 20, and a second wire/coil 30. The body 10 is formed by an elongate tubular structure. In some embodiments, the body 10 itself can be made with an inherent curvature or coiling, while in other embodiments, the body 10 can be formed generally straight. In each embodiment, the body 10 is made of or includes a flexible or bendable material, for example, ePTFE, such that insertion of a more rigid core, for example, the wires/coils 20, 30, into the body 10 will cause the body 10 to assume or adapt to the shape of the core. In some embodiments, the body 10 is constructed as an ePTFE extrusion that is formed with one or more lumens extending longitudinally through it. The body 10 can have a cross-section diameter ranging from 0.4 mm to 0.85 mm, or more specifically from 0.6 to 0.85 mm, or in an exemplary embodiment, 0.8 mm. Referring to the cross-section of the body 10 shown in FIG. 7, the body 10 has a dual lumen arrangement, with a first lumen 14 and a second lumen 16 that are aligned in one direction across the cross-section, although in other embodiments, the lumens 14, 16 can be positioned and extend through the body 10 in other arrangements. The lumens 14, 16 can be formed during extrusion of the body 10, or can be cut into the body 10 after the body 10 has been formed. Lumen 14 is smaller than lumen 16 (but other sizes and equal sizes are also possible). The diameter of smaller lumen 14 can range from 0.5 to 4 mm. The diameter of lumen 16 can range from 0.5 to 4 mm, and have a larger cross-section diameter than lumen 14. In one embodiment, the body 10 has a 2.2 mm diameter, while the lumen 14 has a 0.6 mm inner diameter and the lumen 16 has a 1.0 mm inner diameter. More generally, the one or more lumen formed in the body 10 will be sized and shaped to receive corresponding wires (e.g., wires/coils 20, 30) adapted to be inserted into the body 10. The wires can have a cross-section diameter or thickness that is 0.5 mm to 4 mm, and the diameter/thickness of the wire can be smaller than the cross-section diameter/thickness of the lumen through which it is to be inserted. In one embodiment, the cross-sectional diameter/thickness of wire 20 which can be inserted into lumen 14 can be 0.5 to 4 mm in diameter/width, and the cross-section diameter/thickness of wire 30 can be 0.5 to 4 mm in diameter/width, to be inserted into lumen 16. The cross-section diameters/dimensions of each of the lumens can be at least as great as or greater than the cross-section diameter of the wire being inserted into the lumen. Optionally, the lumen can stretch or expand to accommodate a larger wire cross-section.

Referring back to FIG. 6, the docking device 1 further includes a first wire/coil 20 and a second wire/coil 30. The body 10 and wires 20, 30 are shown in FIG. 6 as turning or wrapping in a counter-clockwise direction from top to bottom (or in an inflow to outflow direction), but the body 10 and wires 20, 30 can also be configured to turn/wrap in a clockwise direction. The wires 20, 30 can each be made of or include one or more shape memory materials, such as NiTi, and can be shape set, for example, to form coils with differently sized curvatures. Other shape memory metals can be used. Non-shape memory materials can also be used, such as stainless steel. The first wire 20 is shape set to form a coil having a larger inner curvature or coil diameter compared to the second wire 30, for example, ranging from 20 to 40 mm, or more specifically, 35 mm, and can be made to have a thinner cross-sectional thickness than the second wire 30, for example, 0.5 mm, or alternatively or in addition to having a thinner cross-section, can be formed with a lower modulus of elasticity than the second wire 30. Meanwhile, the second wire can be shape set to form a coil with a smaller inner curvature or coil diameter than the first wire 20, for example, ranging from 15 to 30 mm, or more specifically, from 20 to 30 mm, or more specifically, 25 mm, while having a larger cross-sectional thickness, for example, 0.8 mm, and/or a higher modulus of elasticity than the first wire 20.

Referring now to FIG. 8, the body 10 of the docking device 1 only has the first wire 20 inserted therein, and extending, for example, through lumen 14, while lumen 16 remains empty. This arrangement defines a first stage or configuration of the docking device 1. In some embodiments, insertion of the first wire 20 can be from either end of the body 10, while in other embodiments, one end of the lumen 14 can be closed, such that insertion of the first wire 20 can only be from one side of the body 10. Initial insertion of the first wire 20 through body 10 causes the body 10 to substantially assume the shape and size of the first wire 20 or a shape having a diameter that is less than an initial diameter of the body, but that can be equal to, more than, or less than an initial diameter of the first wire 20. In one example, the body 10 in the instant example assumes a coil shape with an inner diameter of about 35 mm. This larger initial size of the docking device 1 is maintained during advancement of the docking device 1 around the native anatomy (e.g., mitral anatomy, tricuspid anatomy, etc.) to a desired position relative to the native valve, in order to assist in easier navigation around and capturing of the native anatomy (e.g., mitral anatomy, tricuspid anatomy, etc.). The thinner thickness and/or lower modulus of elasticity of the wire 20 also allows the docking device 1 to be more flexible in the first configuration, which also makes it easier to navigate the distal end of the docking device 1 through and/or around the leaflets, chordae tendineae, and/or other anatomical geometry.

In some embodiments, a proximal region of the first wire 20 can further be shape set to form a coil having a larger diameter than other portions of the first wire 20, for example, 55 mm (not shown). This enlarged proximal region of the first wire 20 would correspond to a portion of the docking device 1 that is positioned in a first chamber of the heart (e.g., the left atrium, right atrium, etc.) when the docking device 1 is advanced to a desired position at the native annulus (e.g., mitral annulus, tricuspid annulus, etc.), and can help reduce or prevent sliding or other migration of the docking device 1 into a second chamber of the heart (e.g. into the left ventricle, right ventricle, etc.) after placement, for example, by sitting at the bottom of the first chamber (e.g., left atrium, right atrium, etc.) and forming an abutment against a floor of the first chamber (e.g., left atrium, right atrium, etc.), or by pressing against the lateral walls of the first chamber (e.g., lateral atrial walls, etc.).

After the docking device 1 has been advanced around the native anatomy (e.g., mitral anatomy, tricuspid anatomy, etc.) to a desired position while in the wider first configuration, the second wire 30 can be inserted into the body 10, for example, through a proximal opening of the larger lumen 16, to adjust the docking device 1 to a smaller second state or configuration. The first wire can be removed from the body 10 prior to or after inserting the second wire, or the first wire can remain in the body 10 with the second wire. Where the first and second wire are both in the body 10, due to the greater thickness and/or higher elastic modulus of the second wire 30, the tension that the second wire 30 applies to the body 10 is greater than and overcomes the tension that the first wire 20 applies to the body 10. As a result, the body 10 is urged by the second wire 30 to assume or get closer to the smaller shape set dimensions of the second wire 30. The inner space 12 of the docking device 1 therefore assumes a smaller functional diameter (which can be equal to, more than, or less than the diameter of the second wire coils; for example, it can assume an approximately 25 mm inner diameter) based on the shape set size of the second wire 30.

Figure 9:
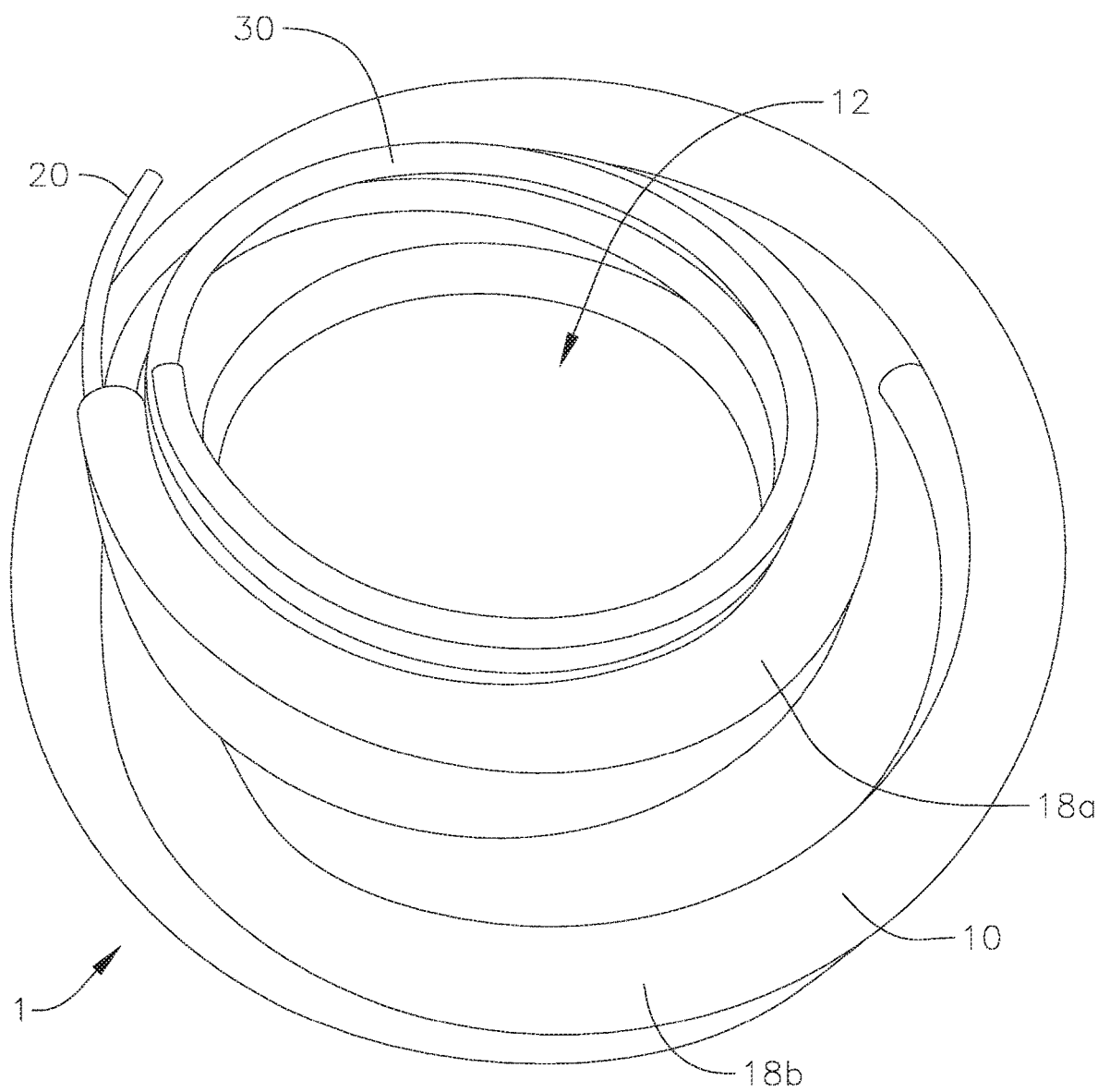
FIG. 9 shows a perspective view of the docking device of FIG. 6, where a wire is partially inserted into the tubular body of the docking device during an adjustment of the docking device from the first size to a second size.

FIG. 9 shows a perspective view of the docking device 1, where the second wire 30 has been partially inserted into the body 10 during an adjustment or transition of the docking device 1 from the first configuration to the second configuration. As can be seen in FIG. 9, a size of a top or proximal portion 18a of the body 10, into which the second wire 30 has already been advanced, has been brought down or reduced to a smaller diameter. Meanwhile, a size of a bottom or distal portion 18b of the body 10 remains at the larger diameter corresponding to the size of the first wire 20, since the second wire 30 has not yet reached and does not yet extend through the distal portion 18b.

Figure 10:
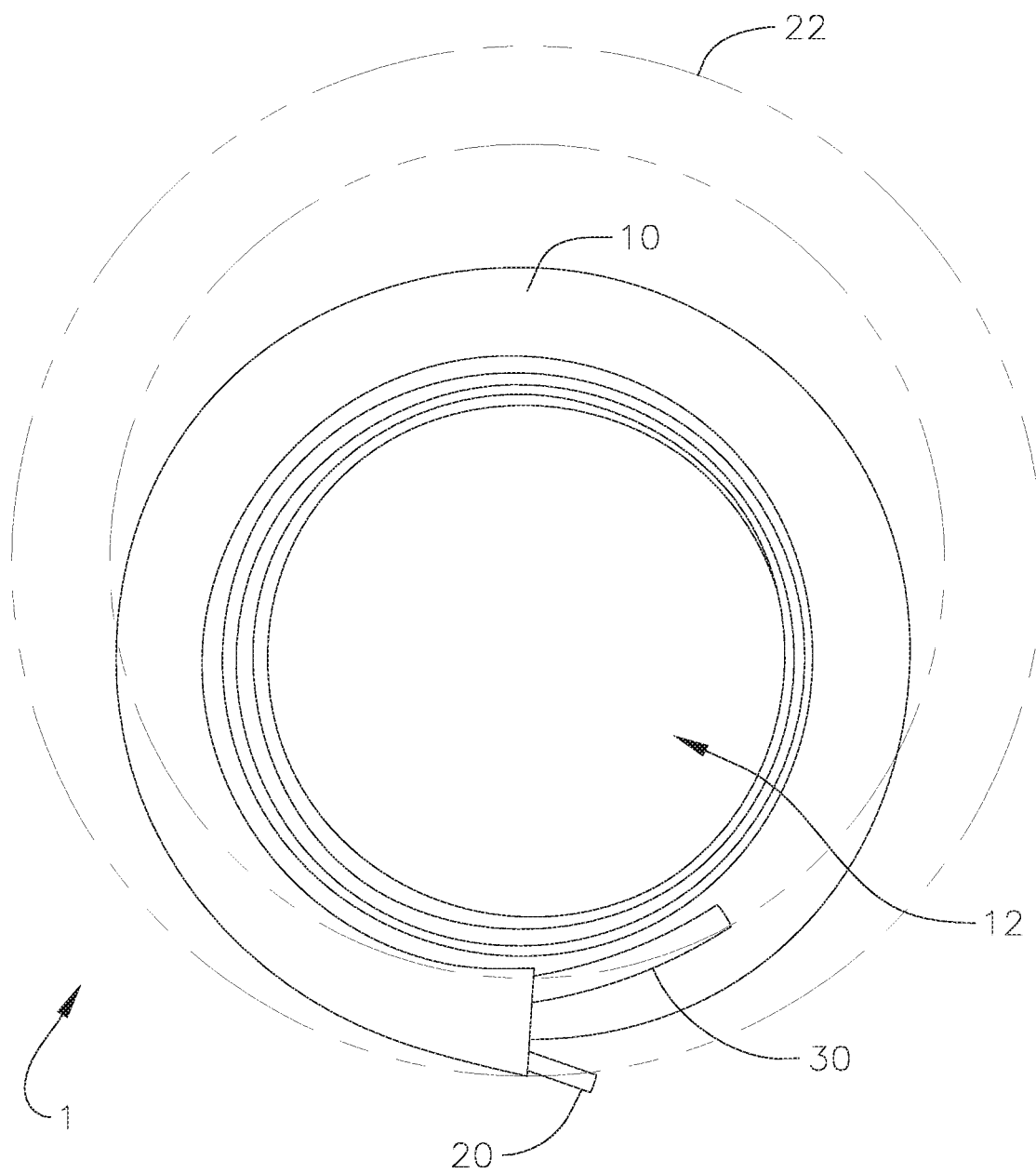
FIG. 10 shows a top perspective view of the docking device of FIG. 6, after the docking device has been adjusted to the second size.

FIG. 10 shows a top perspective view of the docking device 1, where the second wire 30 has been fully inserted into the body 10, and where the docking device 1 has therefore been completely adjusted to the second size configuration. In one example, the docking device 1 assumes a coiled shape with an inner diameter of approximately 25 mm. Meanwhile, for size comparison, dashed lines 22 are also shown in FIG. 10 to show the original coil size (e.g., a 35 mm coil size) of the docking device 1 when the docking device 1 was in the first size configuration.

In other embodiments, the coils of a docking device can change shape by having a tension wire attached to the distal end, as described in U.S. Provisional Patent Application Ser. No. 62/395,940 and U.S. patent application Ser. No. 15/682,287 both of which are incorporated herein by reference in their entirety. Pulling on the tension wire increases the tension and tightens the coils of the docking device.

As discussed above, in order for the prosthetic heart valve to generate a sufficient amount of retention force and/or frictional forces against the docking device 1 to effect a secure hold between the components, both with one another and with the native valve anatomy, the diameter of the docking device 1 (or the diameter of inner space 12 or the functional turns/coils of the docking device) should be smaller than an outer diameter of the prosthetic valve in its expanded state. The relative diameters of the valve and the docking device 1 (e.g., inner space 12 or the functional turns/coils) are important as they directly control the retention forces that are generated between the components when the valve is expanded, where a smaller coil diameter of the docking device 1 will generally lead to a larger retention force between the parts. Therefore, a second wire with an appropriate size should be selected based on a size of the valve to be implanted. In one embodiment, a 25 mm diameter second wire 30 can be used, for example, with a replacement valve with an approximately 29 mm expanded diameter. To effect an even greater retention force, a smaller diameter shape set second wire can be used, for example, a second wire with a 23 mm to 24 mm inner space diameter. In addition, in other procedures where different sized valves are used (e.g., based on different patient anatomies or needs), other differently sized second wires can be selected and used instead.

By inserting two separate wires 20, 30 into the body 10, the spring force of the entire docking device 1 is also increased when the docking device 1 is in the second configuration (e.g., equal to the sum of the spring force of individual wires 20, 30), for example, when compared to other docking devices that have only a single wire core. By better holding a spring shape of the combined docking device 1, the docking device 1 can also improve the retention of the docking device 1 at a desired position relative to the native valve before the prosthetic valve is delivered, for example, by more tightly sandwiching leaflets and other anatomy between coils of the docking device and/or between the coils of the docking device and the prosthetic valve, thereby reducing unintended migration of the docking device 1 (e.g., towards the left ventricle or another chamber).

Similarly as discussed with respect to the first wire 20 above, in some embodiments, a proximal region of the second wire 30 can also further be shape set to have a larger diameter than other portions of the second wire 30 (not shown). This can be done to further hold the docking device 1 in place and to deter migration of the docking device 1 (e.g., into the left ventricle or an undesired location) after placement. For example, the proximal region of the second wire 30 can be shape set to have an inner space or functional diameter of 55 mm to match a 55 mm diameter of a similar enlarged proximal region of first wire 20, and would serve a similar function, where the enlarged proximal region(s) are positioned in the left atrium and form an abutment against a floor and/or wall of the first chamber of the heart (e.g., left atrium, right atrium, etc.) against further movement of the docking device 1 into the second chamber (e.g., left ventricle, right ventricle, etc.). In some embodiments of the docking device 1 may only have one wire (e.g., wire 20 or 30) with an enlarged proximal region, and not the other. In some embodiments, the docking device 1 can have only one lumen and each of the wires (e.g., two wires) is interested into the same lumen sequentially (e.g., one wire can be removed and the other inserted, or the second wire can be inserted next to the first wire).

Figure 7A:
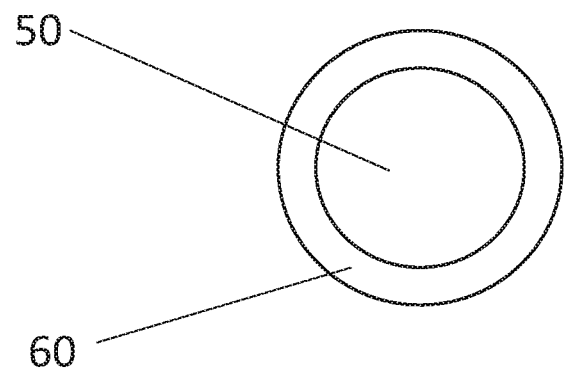
FIG. 7A shows a cross-sectional view of an exemplary embodiment of a docking device.

Various other modifications can be made to the above described embodiments, while still providing for a two-stage adjustable docking device that facilitates both easier delivery of the docking device itself and a more secure docking site for a prosthetic valve. For example, as illustrated in FIG. 7A, rather than having a body with two lumens for holding two separate wires, similar performance can be achieved by first advancing a wire core 50 to a desired position at the native valve site, and then advancing a stiffer tube 60 over the wire. In such an example, the wire can be made of or include a shape memory material such as NiTi, and can be shape set to have a relatively larger coil diameter for initial delivery to the valve site. The wire can also be made relatively thin and/or flexible. Meanwhile, the tube can also be made of or include a shape memory material such as NiTi, can be shape set to have a smaller coil diameter than the wire, and can be made thicker and/or stiffer than the wire, such that the shape of the tube can overcome any resiliency in the shape of the wire. After the wire is advanced to a desired position at the valve site, the tube can be slid or otherwise advanced over the wire to reduce the size of the coil assembly, such that an inner space defined by the coiled shape of the combined docking device assumes a smaller final inner diameter for receiving the prosthetic valve.

In one embodiment, a tube can first be advanced at the valve site, and then a wire can be inserted into the tube to reduce a size of the combined assembly. The tube can be made of or include, for example, a thermoplastic that is co-extruded with an ePTFE lumen, and that can assume a shape that can more easily be maneuvered around the mitral or other valve anatomy. After the tube is advanced to a desired position at the valve site, a wire that is made of or includes a shape memory material such as NiTi can be inserted into the tube. The wire can be shape set to have a coil shape with a relatively smaller diameter compared to the tube, and can be made thicker and/or otherwise stiffer, so that when the wire is inserted into the tube, the wire is sufficiently strong to affect the shape of the tube and to reduce the combined docking device to a smaller coil size for receiving the prosthetic valve. The diameter of the circular turns of a second wire coil inserted into the tube of the docking device can be smaller than the diameter of the circular turns of the first wire coil. The diameter of the first coil wire can range from just as big as the second wire coil diameter to ten times the diameter of the second wire coil. The first wire coil can have a diameter that is twice as big as the diameter of the second coil, four times as big, or ten times as big.

The force applied by the coil is relative compared to the outward force applied by a replacement valve once the replacement valve has expanded. The replacement valve can be an Edwards SAPIEN 3 transcatheter heart valve, or it can be another replacement heart valve. The radial force of the docking device can be five (5) to twenty (20) times that of an expanded replacement valve. The radial force of the docking device can be five (5) to ten (10) times that of the expanded replacement valve.

The sizes and shapes of the tubes, wires, and other components described in the above embodiments are only examples, and different sized components can be selected for both advancement of the docking device to the valve site as well as for final docking of a replacement valve, based for example, on different sized patient anatomies and replacement valves selected, among other factors.

In embodiments of the invention where a docking device is deployed in a two-stage process similar to that described above, delivery of the docking device can be more easily facilitated, and performance of the docking device can be improved. Delivery of a distal end of the docking device into a chamber of the heart (e.g., the left ventricle, right ventricle, etc.) while the docking device is in a larger and more flexible first configuration allows for easier navigation through and/or around the native valve anatomy. Then, adjustment of the docking device to a second configuration where the docking device has a smaller inner diameter and/or an increased spring force provides for a stronger and more secure docking site for a prosthetic valve that is expanded and/or otherwise held in the docking device.

As described with respect to alternative embodiments of the docking device 1 above, in some instances, an atrial or proximal side of a coiled or spiral docking device can be enlarged, for example, to a size that is similar to the anatomy of an atrium. The proximal or atrial coil can be enlarged to a range of 30 mm to 80 mm, or to a range of 30 mm to 75 mm, or to approximately 55 mm, to prevent or block the docking device from movement towards the left ventricle or right ventricle. The enlarged portion of the docking device can abut against a floor of the atrium (e.g., left atrium or right atrium) or push against lateral atrial walls, thereby steadying or stabilizing the docking device relative to the native anatomy (e.g., mitral anatomy, tricuspid anatomy). The atrial, or proximal portion, of the coil can be referred to as the stabilization turn/coil or the atrial turn/coil.

However, in embodiments where a main coil is enlarged at the atrial or proximal end, such enlargement of the main coil of the docking device can result in a less stable connection between the docking device and the prosthetic valve, for example, due to a reduction in the contact area between the components, at least in regions where the docking device has an enlarged region/turn. For example, a transcatheter heart valve that has a 29 mm expanded and unbiased diameter can be docked in a coiled anchor with a 23 mm to 24 mm inner diameter to generate a sufficient retention force between the components after the replacement valve is expanded in the docking device. However, when a portion of the docking device is expanded to 55 mm, the enlarged portions of the docking device may no longer contribute to retention of the replacement valve therein.

Figure 11:
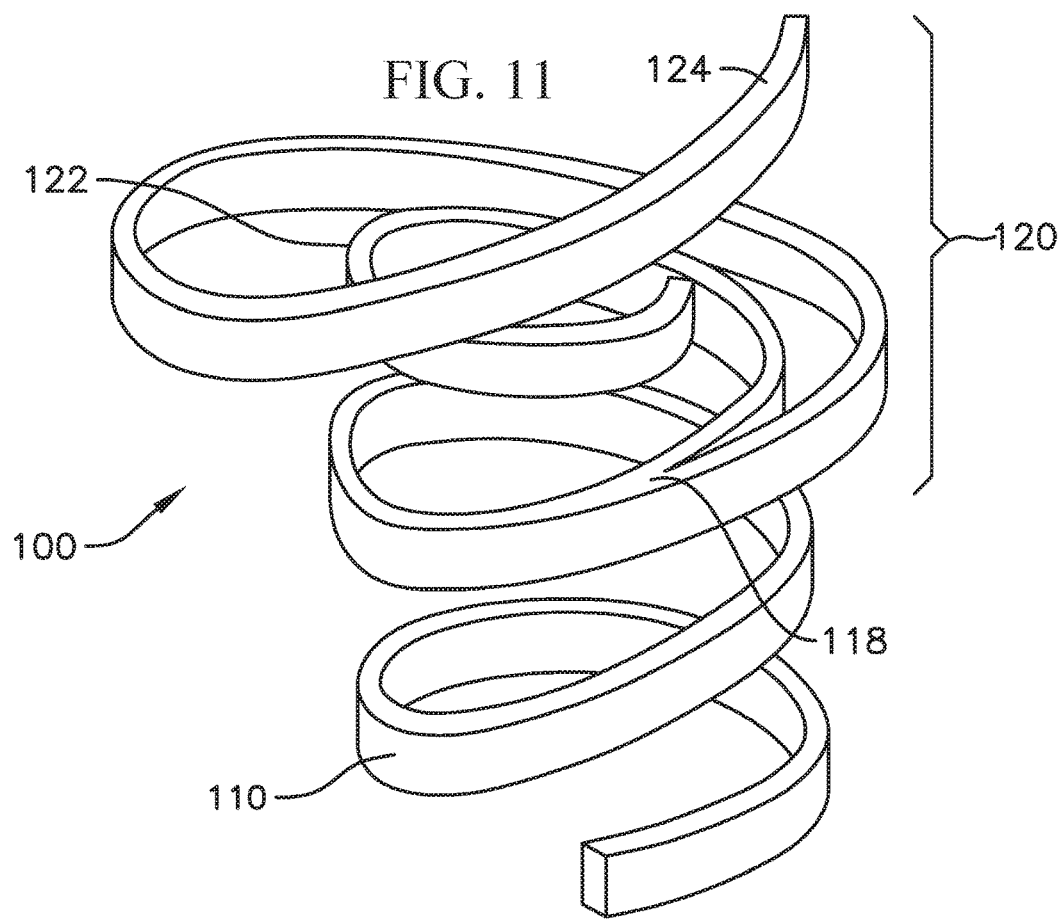
FIG. 11 shows a perspective view of an exemplary docking device.
Figure 11A:
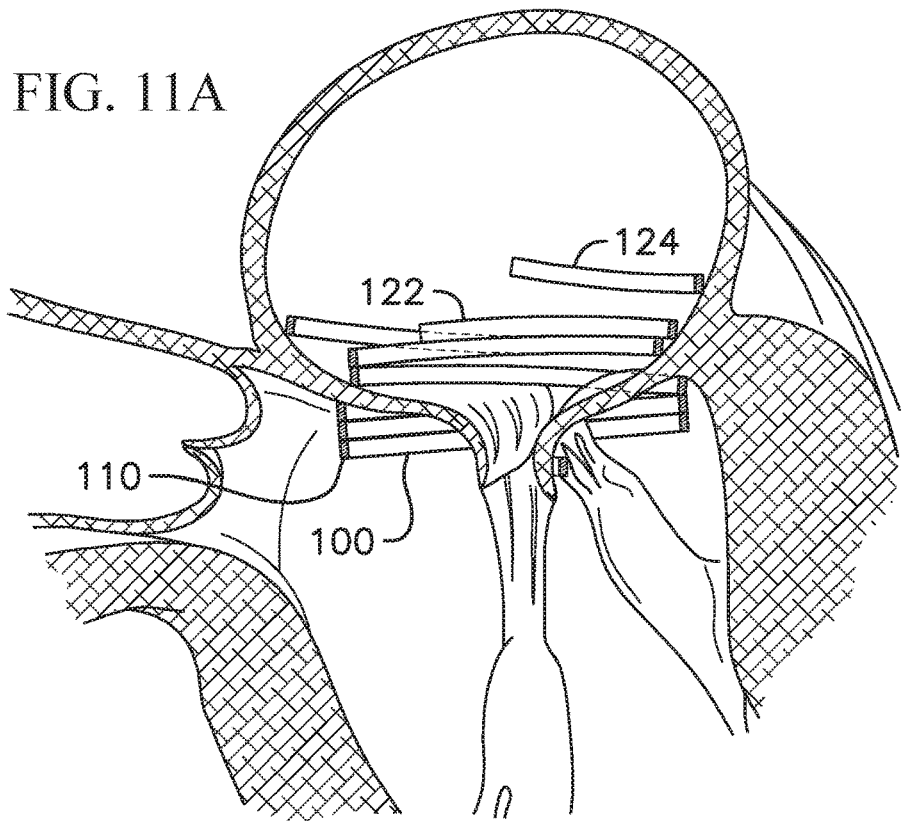
FIG. 11A shows a cross-sectional view of a portion of a heart with the docking device of FIG. 11 positioned at the native mitral annulus.

FIG. 11 shows a perspective view of an exemplary docking device, and FIG. 11A shows a cross-sectional view of the docking device of FIG. 11 positioned at a native mitral annulus of a heart. The docking device 100 includes a distal or ventricular portion 110 made up of a single coil, and a proximal or atrial portion 120 with a first inner coil 122 and a second outer coil 124 (which is configured as a stabilization turn/coil). The coils/turns of this docking device (and the other docking devices described herein) can be configured to turn/wind in a clockwise or counter-clockwise direction. The distal portion 110 and the inner coil 122 of the proximal portion 120 together form a main coil of the docking device 100 that has a substantially constant inner diameter and that forms a docking site for a prosthetic valve. When a 29 mm prosthetic valve is used, for example, for a mitral valve replacement, an embodiment of the docking device 100 can be formed to have a small and substantially constant winding inner diameter of about 23 mm to 24 mm to tightly and securely hold the prosthetic valve after the prosthetic valve is deployed. Other embodiments can have coils with inner diameters that are less than 23 mm or more than 24 mm, depending for example, on the size of the prosthetic valve and on an amount of retention force desired, among other factors.

Meanwhile, the outer coil 124 of the proximal portion 120 serves as a secondary coil that emerges from the main coil to form a separate spiral or coil structure. The outer coil 124 extends around an outside of the inner coil 122, and extends radially outwardly wider than both the inner coil 122 and the distal portion 110 of the docking device 100. As can be seen in FIG. 11A, the outer coil 124 and the inner coil 122 are both configured to extend into a chamber or atrium of the heart (e.g., the left atrium or right atrium) when the docking device 100 is advanced to a desired position relative to the native valve (e.g., mitral valve, tricuspid valve), and is sized and shaped to be sufficiently large or wide to effectively serve as a transient anchoring and stabilizing mechanism (or stabilization coil/turn) for the docking device 100 prior to delivery of the prosthetic valve. In the embodiment of FIGS. 11 and 11A, the outer coil 124 is integrally formed with the distal portion 110 and the inner coil 122 of the proximal portion 120, and extends away from the main coil of the docking device 100 at or near a middle or central region of the docking device 100, forming a fork or split 118 in the docking device 100.

In some embodiments, a position of the split/fork 118 of the docking device 100 corresponds substantially to or can be just proximal to a portion of the docking device 100 that passes through the native valve (e.g., mitral valve, tricuspid valve, etc.) when the docking device 100 is delivered to the native valve. The larger or wider shape and dimensions of the outer coil 124 can form an abutment that blocks or prevents advancement or migration of the docking device 100 (e.g., towards the left ventricle, right ventricle, etc.). In some embodiments, the outer coil 124 can also be wide enough to push radially outwards against lateral portions of the atrial wall, thereby providing further stability to the docking device 100.

Figure 12:
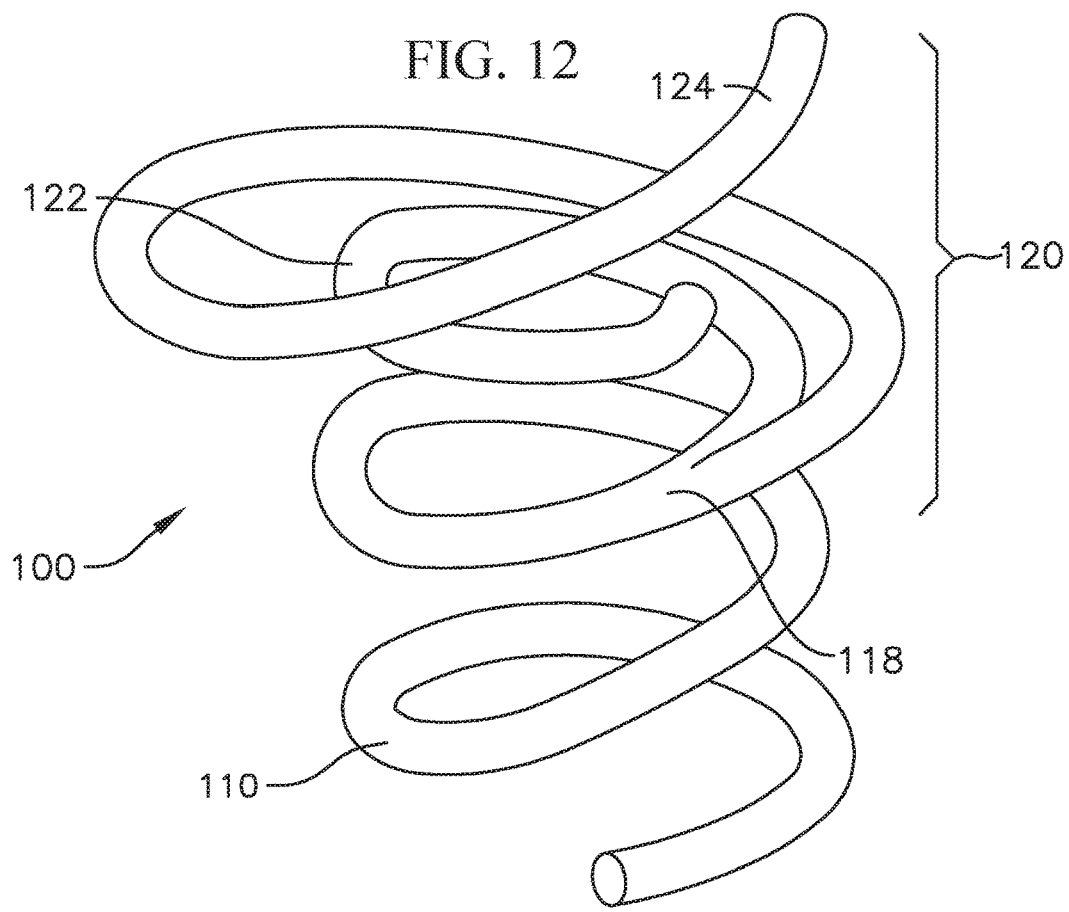
FIG. 12 shows a perspective view of an exemplary docking device.
Figure 12A:
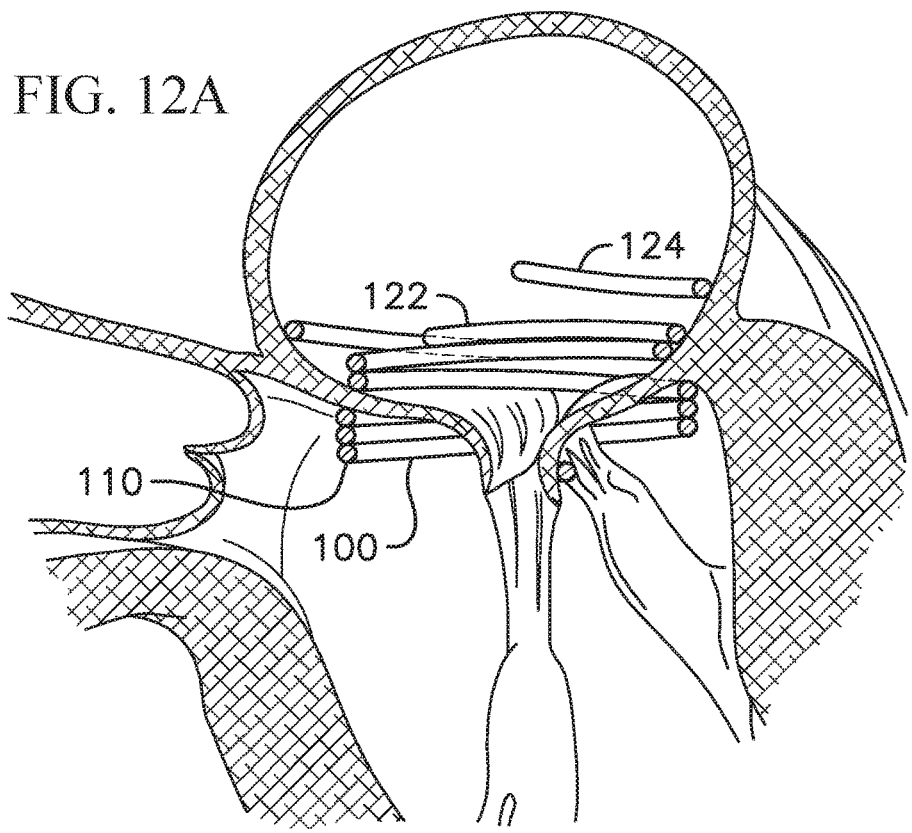
FIG. 12A shows a cross-sectional view of a portion of a heart with the docking device of FIG. 12 positioned at the native mitral annulus.

FIGS. 12 and 12A illustrate an embodiment similar to that in FIGS. 11 and 11A, but instead of a rectangular cross-section as in FIGS. 11 and 11A, the cross-sections of the inner coil 122 and outer coil 124 in the proximal portion, and the distal portion 110, are circular.

FIG. 13 shows a perspective view of an exemplary docking device. The docking device 200 in FIG. 13 can have a same or similar general gross geometry as the docking device 100 in FIGS. 11, 11A, 12, and 12A, but is instead constructed using a first coil 210 and a separate second coil 220.

The first coil 210 serves as a main coil for the docking device 200, and can have size and shape properties similar to the main coil of the docking device 100 in FIGS. 11, 11A, 12, and 12A (e.g., the first coil 210 can have a substantially constant inner diameter of about 23 mm to 24 mm). The first coil 210 provides a main docking site for the prosthetic valve, and can therefore be made thicker and/or more rigid compared to the second coil 220.

Meanwhile, the second coil 220 serves as a secondary coil for the docking device 200, and begins and is secured to or otherwise attached to the first coil 210 at or near a distal or ventricular end 202 of the docking device 200. In the embodiment shown, the two coils 210, 220 of docking device 200 start at approximately the same point at the distal end 202 of the docking device 200. In other embodiments, the two coils may not extend a same length in the distal direction, for example, the second coil 220 may not extend as far distally as the first coil 210. The second coil 220 then splits from and extends away from the first coil 210 at or near a middle or central region of the docking device 200. The two coils 210 and 220 can be connected together in a variety of ways, e.g., by weld, adhesive, or bonded together, or connected by a heat shrink method. In another embodiment, the two coils 210 and 220 can be from the same piece, where the second coil 220 is cut away from the main piece, and the main piece is the first coil. The second coil 220 is configured as a stabilization coil/turn to temporarily anchor and stabilize the docking device 200 at the implantation site prior to delivery of the prosthetic valve. Since the second coil 220 is not used as a docking site for the prosthetic valve, the second coil 220 can be constructed thinner and/or more flexible or floppy when compared to the first coil 210. The additional flexibility in the second coil 220 can also potentially help better stabilize the docking device 200, for example, by allowing the shape of the second coil 220 to better conform to a shape of the surrounding anatomy (e.g., to atrial walls) it comes into contact with, and/or by acting as a damping element against movement of the docking device 200 relative to the native valve annulus.

FIG. 14 shows a perspective view of an exemplary docking device. The docking device 300 in FIG. 14 also has a first coil 310 and a second coil 320. The first coil 310 serves as a main coil for the docking device 300 and as a main docking site for the prosthetic valve. Therefore, similarly as seen with the docking device 200 in FIG. 13, the first coil 310 of the docking device 300 can also be made thicker and/or more rigid compared to the second coil 320.

Meanwhile, the second coil 320 acts as a secondary coil for the docking device 300, and is configured as a stabilization coil/turn to temporarily anchor and stabilize the docking device 300 relative to the native valve prior to delivery of the prosthetic valve. However, unlike in previous embodiments, the second coil 320 is attached to the first coil 310 at or near a proximal or atrial end 304 of the docking device 300, where the proximal ends of the two coils 310, 320 can be crimped or welded together, or otherwise connected to one another, at a connection portion or region 330.

In addition, the second coil 320 is not connected to and does not extend together with the first coil 310 for any appreciable distance along the length of the docking device 300. Instead, the second coil 320 splits from the first coil 310 at or near the proximal end 304 of the docking device 300, near where the two coils 310, 320 are connected. From the proximal end 304 of the docking device 300, the second coil 320 extends in a coil or spiral shape towards a distal end 302 of the docking device 300, and extends radially outwardly wider than the first coil 310. The second coil 320 is shorter axially than the first coil 310, and has a distal end 322 that terminates at or near a middle or central region of the docking device 300 as a whole, which can in some embodiments correspond substantially to a height at which the floor of a chamber or atrium of the heart (e.g., the left atrium or right atrium) will be positioned when the docking device 300 is delivered to the native valve. In this manner, the distal end 322 of the second coil 320 can, in some embodiments, abut against the floor of the chamber or atrium (e.g., left atrium or right atrium) to prevent or hinder movement of the docking device 300 towards another chamber or ventricle (e.g., the left ventricle or right ventricle). In addition, the second coil 320 can be made thinner and/or more flexible or floppy than the first coil 310, to potentially further aid in stabilizing and/or damping movement of the docking device 300 at the implant site prior to delivery of the prosthetic valve.

With respect to the docking devices 200, 300 described with respect to FIGS. 13 and 14, and to other docking devices that utilize two separate coils, as noted above, the two coils can be the same or vary in thickness from one another based on the particular usage of the coil, and can in some embodiments also vary in material, cross-sectional shape, and/or other physical properties, depending on the particular applications and needs. In addition, the connections between the coils can be achieved by crimping, for example with a crimp tube, by welding, adhesion, or by any other appropriate connecting or joining technique.

According to embodiments of docking devices having an integrated or connected double coil, a secondary coil of the double coil can help temporarily anchor and/or stabilize the docking device prior to expansion or docking of a prosthetic valve therein, by pushing or abutting against the atrial floor and/or lateral atrial walls, thereby reducing relative motion between the docking device and the surrounding native tissue. In this manner, abrasions and/or tears of the native valve leaflets and other valve anatomy caused by relative motion or rubbing between the native tissue and the docking device can be reduced or prevented. At the same time, by virtue of the double coil, a main coil of the double coil, including portions of the main coil positioned in the left atrium, remain and retain a small inner diameter, in order to continue to provide an effective docking site for the prosthetic valve along a greater length of the docking device.

Other ways exist to change the size of the coil of the docking device. In another embodiment, the docking device can be a laser hypo tube with a wire run through it, as described in U.S. Provisional Application Ser. No. 62/395,940 and U.S. patent application Ser. No. 15/682,287 both of which are incorporated in their entirety by reference herein.

In another embodiment, the coil can be a shape memory metal that changes shape when its temperature increases.

Various other modifications can also be made to the described embodiments. For example, the docking devices can be covered in an additional layer such as a fabric or textile to reduce damage to the native tissues. A cover that is made of or includes, for example, a high friction material that generates additional frictional forces, to increase retention forces between the docking device and a docked prosthetic valve can be included. The use of a high friction material for the cover provides an increased amount of friction generated between the valve and the covering to hold a shape of the docking device and prevent the docking device from unwinding when the expandable valve is expanded in the docking device.

Figure 15:
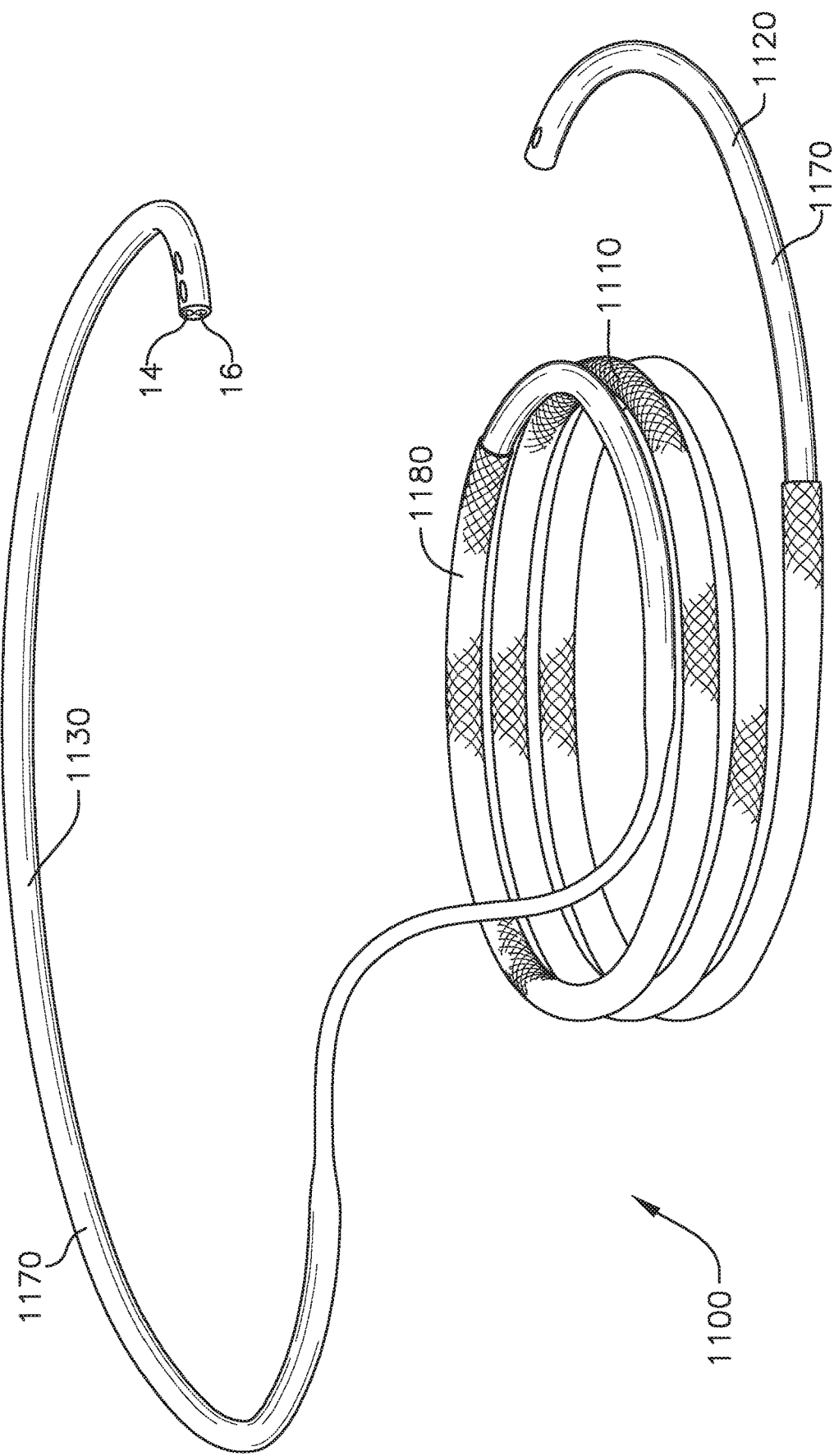
FIG. 15 shows an exemplary docking device including a high-friction covering.

As illustrated in FIG. 15, a cover 1180 that can be made from one or more high friction materials that can be placed over the tubular body 1130. In one embodiment, the cover 1180 is made of or includes a PET braid. The ePTFE tubular body is porous, providing a cushioned, padded-type layer for struts or other portions of a frame of the expandable valve to dig into, improving engagement between the valve and the docking device 1100. Meanwhile, the PET layer 1180 provides additional friction against the native valve leaflets when the prosthetic valve is expanded and the struts or other portions of the valve frame apply outward pressure on the docking device 1100. These features can work together to increase radial forces between the docking device 1100 and the valve, thereby also increasing retention forces and preventing the docking device 1100 from unwinding. In other embodiments, the cover 1180 can be made from one or more other high friction materials that covers the tubular body of the docking device 1100 in a similar manner.

Figure 9A:
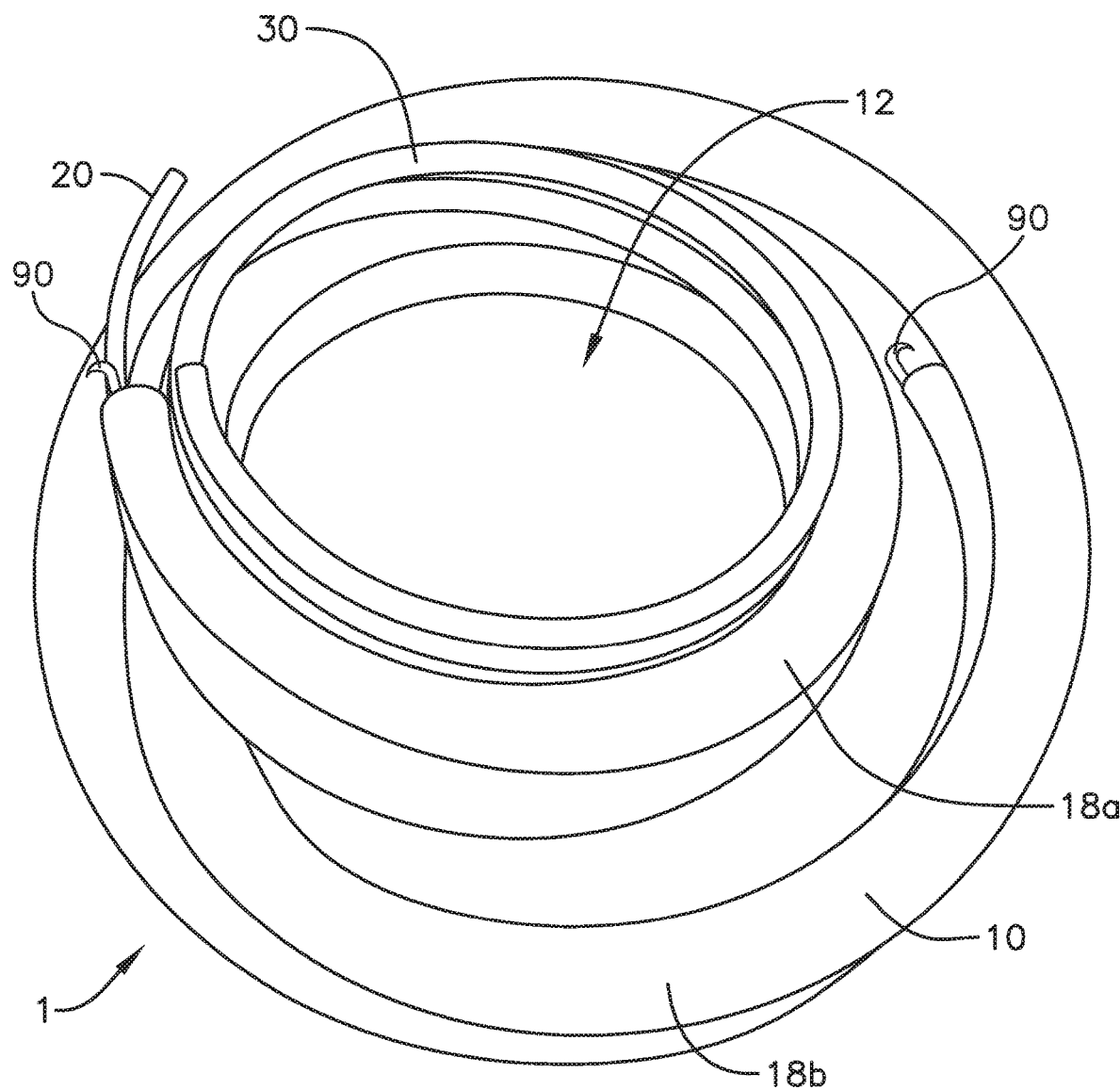
FIG. 9A shows a perspective view of the docking device and anchors.

In still other embodiments, the docking device 1 can also include barbs or anchors 90, as illustrated in FIG. 9A, further increase retention forces. The barbs or anchors 90 can be in the shape of small cleats or hooks or other shape that serves to hold the docking device 1 in place within the native tissue. In an exemplary embodiment, the barbs/anchors 90 extend radially outward from an outer surface and/or the ends of the tubular body of the docking device. In addition, in some embodiments, an outer surface of a frame of the replacement valve can also be covered in a cloth material or other high friction material to further increase the friction force between the docking device and the valve, thereby further reducing or preventing the docking device from unwinding. Once the replacement valve is expanded in the docking device 1100 and the resulting assembly begins functioning as a combined functional unit, any tissue ingrowth can also serve to reduce the load on the combined valve and dock assembly.

The tubular body in some embodiments can also or instead be made of or include a material that promotes more rapid tissue ingrowth, and can be constructed to have a larger amount of surface area, for example, with a VALURE™ film, to further bolster tissue ingrowth. The tubular body can be made from ePTFE and can be constructed with, for example, a 30 micron pore size, to facilitate easier anchoring of blood cells in and against its outer surface, for example, to promote in-growth of tissue after implantation. The pores can range from 30 to 100 microns in size, to increase the surface area for cells to embed within and to increase tissue growth. Furthermore, ePTFE is also a very low friction material that is useful with respect to preventing or minimizing trauma to tissue with which it comes into contact. Tissue growth can be promoted by using a material with a high surface area or by increasing the available surface area for ingrowth, and an increased surface area can be imparted/included in a variety of ways to promote tissue ingrowth, e.g., with pores, braided material, woven material, etc. In addition, some or all of the features from one or more of the embodiments described above can be combined to form still other docking device embodiments.

It may also be desirable to have some portions of the coil with low friction and other regions to be of a higher friction. A lower friction surface or cover 1170 on the upper and lower coils can assist with deployment and provide a smoother insertion of the docking device 1100 and a higher friction surface in the central region can assist with holding the docking device in place. Therefore, as seen in FIG. 15, an additional braid layer 1180 can be added to the central region 1110 of the docking device 1100. The braided layer or other high friction layer 1180 provides additional friction against the THV when the THV is expanded in the docking device 1100. The friction that is formed at the interfaces between the inner surface of the central region 1110 of the docking device 1100, the native mitral leaflets, and the outer surface of the THV creates a more secure locking mechanism to more strongly anchor the THV and the docking device 1100 to the native annulus. The braid layer can be limited to extend across only the central coils of the docking device 1100 so that the upper region 1130 and lower region 1120 of the docking device 1100 remain lower friction. The braiding can also provide a larger surface area for promotion of tissue ingrowth. While cover 1180, surface/cover 1170, and other features/characteristics are described with respect to device 1100, these can be incorporated in the same or similar ways into the docking devices described elsewhere herein.

Furthermore, embodiments of docking devices have generally been discussed above and examples have been given with respect to anchoring replacement valves at the mitral position. However, as was also mentioned above, the docking devices, as described or slightly modified versions thereof, can also be applied in similar manners to valve replacements at other valve sites as well, for example, at the tricuspid or aortic positions (e.g., to treat insufficiency issues). The docking devices can similarly be made of or include a shape memory material, such as Nitinol, and/or a non-shape memory material. Although the other valve annuli may be rounder or more circular in shape than the mitral valve annulus, patients that are diagnosed with insufficiencies at either position nevertheless exhibit enlarged annuli that both prevent the native leaflets from properly coapting, and that also can cause the annuli to become too large, too soft, or too otherwise diseased to securely hold an expandable valve therein. Therefore, use of a rigid or semi-rigid docking device can also be beneficial for anchoring a replacement valve at those valve sites as well.

When applied to valves other than the mitral valve, docking devices can also provide a more secure landing zone at those sites as well. The docking devices and replacement valves can be applied similarly as has been discussed with respect to implantation at the mitral valve. A possible access point for tricuspid replacement can be, for example, transseptal access, while a possible access point for aortic replacement can be, for example, transfemoral access, although access to the respective valve sites is not limited thereto. The use of coil-shaped docking devices as previously described at the other valve sites also serves to circumferentially cinch or clamp the native leaflets between coils of the docking device after deployment of the replacement valve at the native annulus, which further prevents or reduces slipping or other movement of the docking device and of the sandwiched tissue relative to the docking device, and prevents unwanted growth or expansion of the native annulus over time.

The docking devices described herein can also be used alone to treat the native valve insufficiency. For example the coils described herein can be the final implant to treat tricuspid valve insufficiency. The device can be delivered behind the leaflets and chords in the right ventricle, and reduce the diameter of the orifice. The orifice is reduced since the native tricuspid valve leaflets are attached at the annulus on one side, and the chordae on the ventricular side. Part of the device sits in the right atrium to help anchor or hold the device in place as previously described. The portion that sits in the right ventricle is sized so as to reduce the valve annulus to a desired diameter.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The features and characteristics of one embodiment can be combined with features and characteristics of another embodiment even if not described together above.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods and various steps can be combined in a variety of ways even if not described together above. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather the scope of the disclosure is defined by the following claims.

What is claimed is:

1. A method of implanting a docking device for a prosthetic valve at a native heart valve, comprising the steps of:
    obtaining a docking device comprising a flexible tubular body having a distal end, a proximal end, and a first lumen and a second lumen extending at least partially therethrough, wherein when a first coil having a first diameter is located within the first lumen, the tubular body adopts a first configuration;
    positioning a distal end of a delivery catheter into a first chamber of a heart;
    advancing the tubular body, from within the delivery catheter so that the distal end of the tubular body is advanced between native valve leaflets, and positioned in a second chamber of the heart;
    inserting a second coil comprising a plurality of turns having a second diameter into the second lumen of the docking device, so that the tubular body adopts a second configuration;
    releasing the proximal end of the docking device in the first chamber of the heart;
    inserting a replacement valve in an inner space defined by the tubular body in the second configuration; and
    radially expanding the replacement valve until there is a retention force between the replacement valve and the docking device sufficient to hold the replacement valve in a stable position in the native heart valve.

2. The method according to claim 1, further comprising inserting the first coil into the first lumen to cause the tubular body to adopt the first configuration.

3. The method according to claim 2, wherein the step of advancing the tubular body from within the delivery catheter occurs before the step of inserting the first coil into the first lumen.

4. The method according to claim 2, wherein the step of inserting the first coil into the first lumen occurs before the step of advancing the tubular body from within the delivery catheter, and wherein at least a portion of the tubular body and at least a portion of the first coil are advanced together between the native valve leaflets and positioned in the second chamber of the heart.

5. The method according to claim 2, wherein the step of inserting the first coil into the first lumen occurs before the step of positioning the distal end of the delivery catheter into the first chamber of the heart.

6. The method according to claim 2, wherein the step of inserting the first coil into the first lumen occurs after the step of positioning the distal end of the delivery catheter into the first chamber of the heart.

7. The method according to claim 1, wherein:
    the first diameter is between 20 to 40 mm; and
    the second diameter is between 15 to 30 mm.

8. The method according to claim 1, wherein the first diameter is between 2 to 10 times greater than the second diameter.

9. The method according to claim 1, wherein the first coil further comprises a first plurality of circular turns.

10. The method according to claim 9, wherein the first coil further comprises an upper turn extending in a proximal direction from the first plurality of circular turns, wherein the upper turn of the first coil is configured as a stabilization turn to help prevent migration of the docking device, the upper turn of the first coil defining an upper turn diameter greater than the first diameter.

11. The method of claim 10, wherein the upper turn diameter is between 40 to 100 mm.

12. The method according to claim 1, wherein a proximal end of the first lumen of the docking device is open.

13. The method according to claim 1, wherein a proximal end of the second lumen of the docking device is open.

14. The method according to claim 1, wherein the docking device further comprises a high-friction cover on a portion of the flexible tubular body configured such that slippage of the docking device relative to the native leaflets is inhibited when implanted.

15. The method according to claim 1, wherein the docking device further comprises a covering having a large amount of surface area to promote tissue ingrowth.

16. The method according to claim 1, wherein the flexible tubular body of the docking device is comprised of a co-extruded thermoplastic material.

* * * * *